(12) United States Patent
Ackley et al.

(10) Patent No.: US 9,757,772 B2
(45) Date of Patent: Sep. 12, 2017

(54) INSPECTION SYSTEM

(71) Applicant: Ackley Machine Corporation, Moorestown, NJ (US)

(72) Inventors: E. Michael Ackley, Mannington, NJ (US); Mark Ford, Deptford, NJ (US)

(73) Assignee: Ackley Machine Corporation, Moorestown, NJ (US)

( * ) Notice: Subject to any disclaimer, the term of this patent is extended or adjusted under 35 U.S.C. 154(b) by 0 days.

(21) Appl. No.: 15/271,799

(22) Filed: Sep. 21, 2016

(65) Prior Publication Data
US 2017/0008036 A1    Jan. 12, 2017

Related U.S. Application Data

(60) Continuation of application No. 14/970,961, filed on Dec. 16, 2015, now Pat. No. 9,468,948, which is a
(Continued)

(51) Int. Cl.
*B07C 5/00* (2006.01)
*B07C 5/342* (2006.01)
(Continued)

(52) U.S. Cl.
CPC .............. *B07C 5/3422* (2013.01); *B07C 5/34* (2013.01); *B07C 5/3412* (2013.01); *B07C 5/362* (2013.01);
(Continued)

(58) Field of Classification Search
CPC ................................ B07C 5/34; B07C 5/3422
(Continued)

(56) References Cited

U.S. PATENT DOCUMENTS 1,134,822 A   3/1920   Varble
2,613,594 A   10/1954  King
(Continued)

FOREIGN PATENT DOCUMENTS

CN   1940565       4/2004
DE   3836142 A1   4/1990
(Continued)

OTHER PUBLICATIONS

International Search Report and Written Opinion issued on Sep. 16, 2011 in corresponding International Application No. PCT/US11/38534.
(Continued)

*Primary Examiner* — Terrell Matthews
(74) *Attorney, Agent, or Firm* — Nixon & Vanderhye PC

(57) ABSTRACT

An inspection system is configured for use with a conveyer apparatus including carrier bars. Each carrier bar conveys pellet-shaped articles along a predetermined path. The inspection system includes at least one camera unit for sensing a predetermined characteristic of the pellet-shaped articles, a removal unit, and a controller. The removal unit, downstream from the at least one camera unit, removes selected pellet-shaped article(s) from the carrier bar(s) depending on whether the characteristic is sensed by the at least one camera unit. The controller is in communication with the at least one camera unit and the removal unit. The controller provides a signal to the removal unit in accordance with the sensed characteristic. The removal unit includes a rotatable ejection drum having extended vacuum nozzles along its length, equal to the number of articles conveyed in each carrier bar. Each vacuum nozzle selectively removes article(s) from the carrier bar(s) by suction.

25 Claims, 28 Drawing Sheets

Related U.S. Application Data continuation of application No. 14/799,740, filed on Jul. 15, 2015, now Pat. No. 9,259,766, which is a continuation of application No. 14/293,307, filed on Jun. 2, 2014, now Pat. No. 9,101,962, which is a continuation of application No. 13/740,684, filed on Jan. 14, 2013, now Pat. No. 8,770,413, which is a division of application No. 13/149,140, filed on May 31, 2011, now Pat. No. 8,373,081.

(60) Provisional application No. 61/485,109, filed on May 11, 2011, provisional application No. 61/457,022, filed on Dec. 9, 2010, provisional application No. 61/344,150, filed on Jun. 1, 2010.

(51) Int. Cl.
| | | |
|---|---|---|
| *B07C 5/36* | (2006.01) | |
| *G01N 21/88* | (2006.01) | |
| *G01N 21/85* | (2006.01) | |
| *B07C 5/34* | (2006.01) | |
| *G01N 21/84* | (2006.01) | |

(52) U.S. Cl.
CPC .............. *B07C 5/363* (2013.01); *G01N 21/85* (2013.01); *G01N 21/8806* (2013.01); *G01N 21/8851* (2013.01); *G01N 2021/845* (2013.01); *G01N 2021/8592* (2013.01); *G01N 2201/02* (2013.01); *G01N 2201/062* (2013.01); *G01N 2201/0621* (2013.01); *Y10T 29/49826* (2015.01)

(58) Field of Classification Search
USPC ................ 209/546, 552, 580, 587, 938, 939
See application file for complete search history.

(56) References Cited

U.S. PATENT DOCUMENTS

| | | |
|---|---|---|
| 3,052,552 A | 9/1962 | Koerner et al. |
| 3,084,781 A | 4/1963 | Merrill |
| 3,215,536 A | 11/1965 | Simeone et al. |
| 3,335,658 A | 8/1967 | Uschmann |
| 3,514,803 A | 6/1970 | Turney, Jr. |
| 3,696,924 A | 10/1972 | Sterling |
| 3,735,699 A | 5/1973 | Koelschbach |
| 3,884,143 A | 5/1975 | Ackley |
| 3,889,591 A | 6/1975 | Noguchi |
| 3,948,765 A | 4/1976 | Anschutz |
| 4,082,188 A | 4/1978 | Grimmell et al. |
| 4,235,579 A | 11/1980 | Kurz et al. |
| 4,351,437 A * | 9/1982 | Long .................... A01D 33/04 209/545 |
| 4,371,081 A | 2/1983 | Satake |
| 4,397,871 A | 8/1983 | Meyer et al. |
| 4,444,470 A | 4/1984 | Ioka et al. |
| 4,446,481 A | 5/1984 | Edamatsu et al. |
| 4,519,310 A | 5/1985 | Shimizu et al. |
| 4,528,904 A | 7/1985 | Ackley |
| 4,578,273 A | 3/1986 | Krubert |
| 4,582,201 A | 4/1986 | Taniguchi et al. |
| 4,619,196 A | 10/1986 | Matsuoka |
| 4,630,736 A | 12/1986 | Maughan et al. |
| 4,632,028 A | 12/1986 | Ackley |
| 4,648,053 A | 3/1987 | Fridge |
| 4,670,271 A | 6/1987 | Pasternak |
| 4,672,892 A | 6/1987 | Ackley |
| 4,682,683 A | 7/1987 | Ackley, Sr. et al. |
| 4,699,274 A | 10/1987 | Saika |
| 4,757,382 A | 7/1988 | Kaziura et al. |
| 4,776,466 A | 10/1988 | Yoshida |
| 4,830,194 A | 5/1989 | Kajiura et al. |
| 4,839,497 A | 6/1989 | Sankar et al. |
| 4,843,958 A | 7/1989 | Egosi |
| 4,851,902 A | 7/1989 | Tezuka |
| 4,855,146 A | 8/1989 | Murakami et al. |
| 4,901,865 A | 2/1990 | Staples |
| 4,905,589 A | 3/1990 | Ackley |
| 4,946,046 A | 8/1990 | Affleck et al. |
| 5,019,326 A | 5/1991 | Yaginuma et al. |
| 5,058,175 A | 10/1991 | Aso |
| 5,085,325 A | 2/1992 | Jones et al. |
| 5,085,510 A | 2/1992 | Mitchell |
| 5,135,114 A | 8/1992 | Satake et al. |
| 5,147,047 A | 9/1992 | Ahmed et al. |
| 5,148,923 A | 9/1992 | Fraenkel et al. |
| 5,165,340 A | 11/1992 | Karlyn et al. |
| 5,186,942 A | 2/1993 | Deters et al. |
| 5,220,400 A | 6/1993 | Anderson et al. |
| 5,237,621 A | 8/1993 | Cox et al. |
| 5,305,392 A | 4/1994 | Longest, Jr. et al. |
| 5,339,964 A | 8/1994 | Gray et al. |
| 5,339,965 A | 8/1994 | Klukis et al. |
| 5,351,117 A | 9/1994 | Stewart et al. |
| 5,376,388 A | 12/1994 | Meyers |
| 5,376,771 A | 12/1994 | Roy |
| 5,398,818 A | 3/1995 | McGarvey |
| 5,419,438 A | 5/1995 | Squyres et al. |
| 5,423,252 A | 6/1995 | Yamamoto et al. |
| 5,429,045 A | 7/1995 | Karlyn et al. |
| 5,433,146 A | 7/1995 | Ackley |
| 5,443,164 A | 8/1995 | Walsh et al. |
| 5,505,775 A | 4/1996 | Kitos |
| 5,534,281 A | 7/1996 | Pappas et al. |
| 5,553,536 A | 9/1996 | Vanos |
| 5,558,231 A | 9/1996 | Weier |
| 5,602,646 A | 2/1997 | Bernardin et al. |
| 5,610,710 A * | 3/1997 | Canfield .......... G01N 21/95692 356/136 |
| 5,630,499 A | 5/1997 | Louden et al. |
| 5,638,961 A | 6/1997 | Satake et al. |
| 5,652,432 A | 7/1997 | Yaginuma |
| 5,655,453 A | 8/1997 | Ackley |
| 5,661,249 A | 8/1997 | Rupp et al. |
| 5,669,511 A | 9/1997 | Satake et al. |
| 5,695,043 A | 12/1997 | Maezuru et al. |
| 5,703,377 A | 12/1997 | Ainsworth et al. |
| 5,730,048 A | 3/1998 | Averill et al. |
| 5,735,402 A | 4/1998 | Pezzoli et al. |
| 5,746,323 A | 5/1998 | Dragotta |
| 5,768,996 A | 6/1998 | Ackley |
| 5,794,756 A | 8/1998 | Taylor et al. |
| 5,805,510 A | 9/1998 | Miyakawa et al. |
| 5,819,953 A | 10/1998 | Julius et al. |
| 5,834,047 A | 11/1998 | Ahn |
| 5,836,243 A | 11/1998 | Ackley |
| 5,878,658 A | 3/1999 | Ackley |
| 5,878,868 A | 3/1999 | Gotoh et al. |
| 5,894,801 A | 4/1999 | Ackley |
| 5,957,306 A | 9/1999 | Hoffman |
| 5,979,309 A | 11/1999 | Boyce |
| 6,097,493 A | 8/2000 | Satake et al. |
| 6,130,405 A | 10/2000 | Loringer |
| 6,267,997 B1 | 7/2001 | Ream et al. |
| 6,286,421 B1 | 9/2001 | Ackley |
| 6,314,876 B1 | 11/2001 | Ackley |
| 6,330,351 B1 | 12/2001 | Yasunaga |
| 6,353,203 B1 | 3/2002 | Hokodate et al. |
| 6,359,255 B1 | 3/2002 | Yamamoto et al. |
| 6,390,280 B1 | 5/2002 | Boyce |
| 6,421,159 B1 | 7/2002 | Sutter et al. |
| 6,450,089 B2 | 9/2002 | Ackley et al. |
| 6,541,732 B2 | 4/2003 | Hirose et al. |
| 6,639,167 B1 | 10/2003 | Bjork |
| 6,680,459 B2 | 1/2004 | Kanaya et al. |
| 6,683,970 B1 | 1/2004 | Satake et al. |
| 6,720,567 B2 | 4/2004 | Fordahi et al. |
| 6,727,452 B2 | 4/2004 | Schrader |
| 7,059,478 B2 * | 6/2006 | Spatafora ................ B65B 19/30 131/282 |
| 7,102,741 B2 | 9/2006 | Ackley, Jr. et al. |
| 7,456,946 B2 | 11/2008 | Ackley, Jr. et al. |

(56) References Cited

U.S. PATENT DOCUMENTS

| | | | |
|---|---|---|---|
| 7,541,556 B2 * | 6/2009 | Canepa | B07C 5/3404 |
| | | | 209/524 |
| 7,569,794 B2 | 8/2009 | Faour et al. | |
| 7,701,568 B2 | 4/2010 | Ackley, Jr. et al. | |
| 7,746,486 B2 | 6/2010 | Ferlet | |
| 7,795,556 B1 | 9/2010 | Dean | |
| 7,800,009 B2 | 9/2010 | Gochar, Jr. | |
| 8,285,026 B2 | 10/2012 | Dirix | |
| 8,427,538 B2 | 4/2013 | Ahiska | |
| 8,698,815 B2 * | 4/2014 | Kiuchi | G06T 1/20 |
| | | | 345/502 |
| 8,724,774 B2 | 5/2014 | Langeveld | |
| 8,827,082 B2 * | 9/2014 | Radema | B07C 5/3412 |
| | | | 209/552 |
| 9,117,137 B2 * | 8/2015 | Uchiyama | G06K 9/46 |
| 2003/0035870 A1 | 2/2003 | Ackley, Jr. et al. | |
| 2004/0013778 A1 | 1/2004 | Ackley, Jr. et al. | |
| 2004/0091594 A1 | 5/2004 | Ackley, Jr. et al. | |
| 2004/0094050 A1 | 5/2004 | Ackley, Jr. et al. | |
| 2005/0075261 A1 | 4/2005 | Baeck et al. | |
| 2005/0266123 A1 | 12/2005 | Collins et al. | |
| 2006/0219609 A1 | 10/2006 | Canepa | |
| 2006/0236792 A1 | 10/2006 | Hanna | |
| 2006/0268264 A1 | 11/2006 | Ackley, Jr. et al. | |
| 2007/0187299 A1 | 8/2007 | Valerio | |
| 2008/0158332 A1 | 7/2008 | Ackley et al. | |
| 2009/0059214 A1 | 3/2009 | Ackley et al. | |
| 2009/0090848 A1 | 4/2009 | Ackley, Jr. et al. | |
| 2010/0163467 A1 | 7/2010 | Ackley, Jr. et al. | |
| 2011/0297590 A1 | 12/2011 | Ackley et al. | |
| 2013/0128026 A1 * | 5/2013 | Hirose | G01N 21/8903 |
| | | | 348/125 |
| 2013/0134072 A1 | 5/2013 | Ackley et al. | |
| 2014/0139658 A1 | 5/2014 | Dhanvantri | |
| 2014/0174995 A1 * | 6/2014 | Ang | B07C 3/00 |
| | | | 209/546 |
| 2014/0260104 A1 | 9/2014 | Ackley et al. | |
| 2015/0314334 A1 | 11/2015 | Ackley et al. | |
| 2016/0107198 A1 | 4/2016 | Ackley et al. | |

FOREIGN PATENT DOCUMENTS

| | | |
|---|---|---|
| EP | 0 118 857 | 9/1984 |
| EP | 0442782 A1 | 8/1991 |
| EP | 0596328 A2 | 5/1994 |
| EP | 0919377 A1 | 6/1999 |
| EP | 1 070 959 | 1/2001 |
| FR | 002738638 A1 | 3/1997 |
| JP | 53-32759 | 3/1978 |
| JP | 61-10457 | 1/1986 |
| JP | 62-138279 | 6/1987 |
| TW | 586006 | 5/2004 |
| WO | 81/01232 | 5/1981 |
| WO | 91/01884 | 2/1991 |
| WO | 97/16075 | 5/1997 |
| WO | 00/74938 | 12/2000 |
| WO | 2004/045031 A3 | 5/2004 |

OTHER PUBLICATIONS

International Preliminary Report on Patentability issued on Dec. 13, 2012 in corresponding International Application No. PCT/US11/38534.

Cognex Website (9 pages) with copyright notice of 2001.

Office Action issued on Aug. 26, 2014 in Chinese Application No. 2014082101029960 (with translation), pp. 1-12.

Supplemental Search Report issued on Feb. 21, 2014 in International Application No. PCT/US11/38534, pp. 1-10.

Supplementary Search Report and Opinion issued on Feb. 21, 2014 in corresponding European Application No. 11790275.9.

Office Action issued on Nov. 13, 2015 in Chinese Application No. 201180037926.2 (with translation), 7 pages.

\* cited by examiner

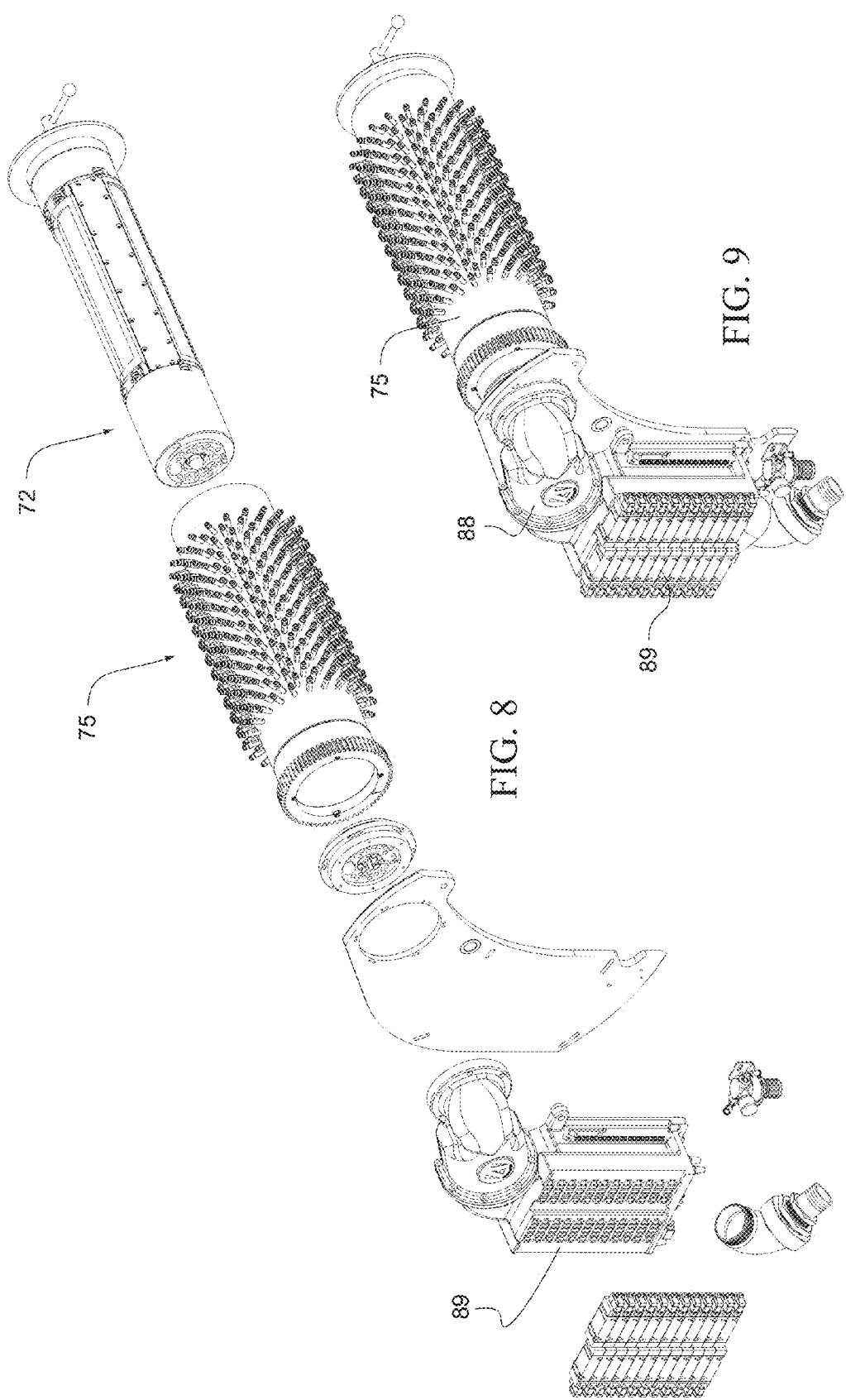

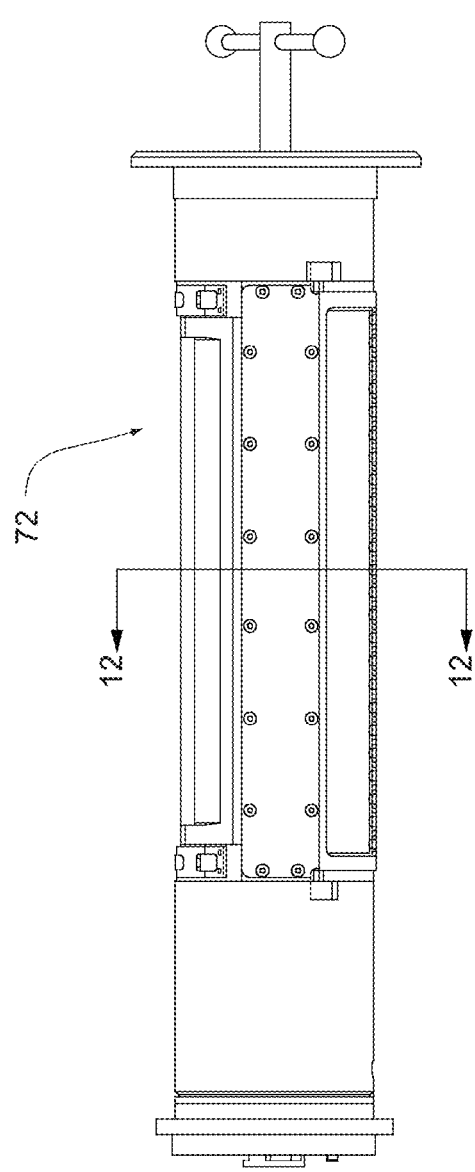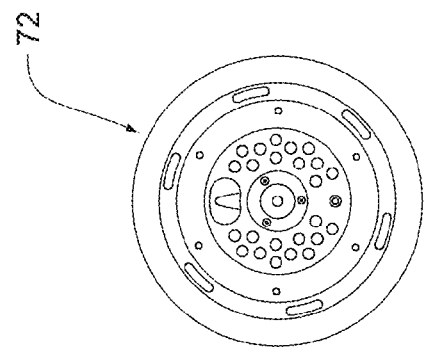
FIG. 11
FIG. 12
FIG. 13

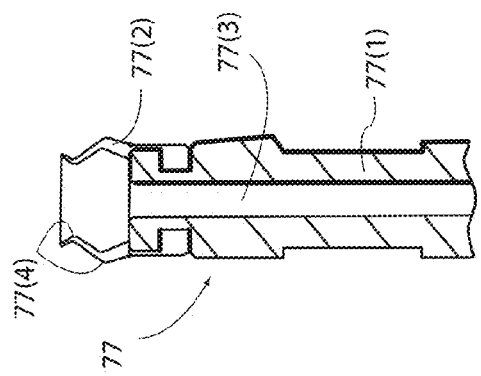
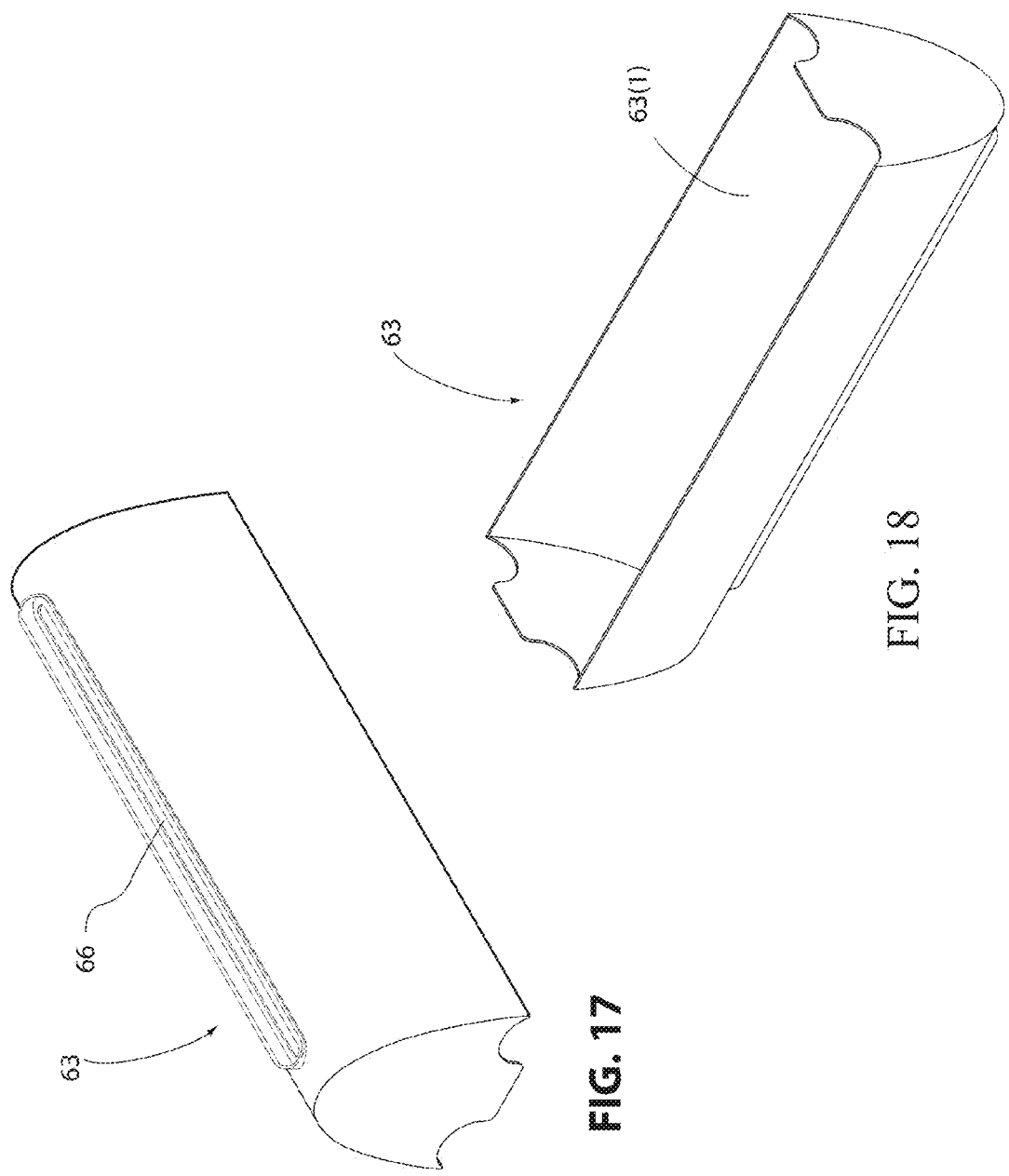

Operation | Setup | Manual Operation | Maintenance | Browser

Commit Changes

Select Level Permissions

| | | | | Permit | Permit | Permit | Permit |
|---|---|---|---|---|---|---|---|
| | | | | Deny | Deny | Deny | Deny |
| Screen | Control | | | Operator | Mechanic | Engineer | Administrator |
| ColorVision | Camera 1 Show Grid Button | Permit | Deny | ☑ | ☑ | ☑ | ☑ |
| ColorVision | Camera 2 Show Grid Button | Permit | Deny | ☑ | ☑ | ☑ | ☑ |
| MainScreen | Browser Screen Select | Permit | Deny | ☑ | ☑ | ☑ | ☑ |
| MainScreen | Fault Status Screen Select | Permit | Deny | ☑ | ☑ | ☑ | ☑ |
| MainScreen | Maintenance Screen Select | Permit | Deny | ☑ | ☑ | ☑ | ☑ |
| MainScreen | Manual Operation Screen Select | Permit | Deny | ☑ | ☑ | ☑ | ☑ |
| MainScreen | Operation Screen Select | Permit | Deny | ☑ | ☑ | ☑ | ☑ |
| MainScreen | Setup Screen Select | Permit | Deny | ☐ | ☐ | ☑ | ☑ |
| MainScreen | Vision Screen Select | Permit | Deny | ☐ | ☐ | ☐ | ☑ |
| Maintenance | Database Management | Permit | Deny | ☐ | ☐ | ☐ | ☑ |
| Maintenance | Log File Aging | Permit | Deny | ☐ | ☐ | ☐ | ☑ |
| Maintenance | Product Tab | Permit | Deny | ☐ | ☐ | ☑ | ☑ |
| Maintenance | Recipe Tab | Permit | Deny | ☑ | ☑ | ☑ | ☑ |
| Maintenance | User Management Functions | Permit | Deny | ☑ | ☑ | ☑ | ☑ |
| Operation | Doctor Blade Auto Button | Permit | Deny | ☑ | ☑ | ☑ | ☑ |
| Operation | Doctor Blade Control | Permit | Deny | ☑ | ☑ | ☑ | ☑ |
| Operation | Doctor Blade Manual Button | Permit | Deny | ☑ | ☑ | ☑ | ☑ |
| Operation | Run, Stop & Idle Buttons | Permit | Deny | ☑ | ☑ | ☑ | ☑ |

Fault Status | Print Inspection Cameras | Color Cameras

Refresh Data | Exit

⊗ Main Belt Drive Fault    ADMIN Logged In: 8:48 AM

FIG. 33

INSPECTION SYSTEM

CROSS-REFERENCE TO APPLICATION

This application is a continuation of application Ser. No. 14/970,961 filed Dec. 16, 2015, now pending, which is a continuation of application Ser. No. 14/799,740 filed Jul. 15, 2015, now U.S. Pat. No. 9,259,766, which is a continuation of application Ser. No. 14/293,307 filed Jun. 2, 2014, now U.S. Pat. No. 9,101,962, which is a continuation of application Ser. No. 13/740,684 filed Jan. 14, 2013, now U.S. Pat. No. 8,770,413, which is a divisional of application Ser. No. 13/149,140 filed May 31, 2011, now U.S. Pat. No. 8,373,081, which claims the benefit of Provisional Application No. 61/485,109 filed May 11, 2011, 61/457,022 filed Dec. 9, 2010, and 61/344,150 filed Jun. 1, 2010, the entire contents of each of which are hereby incorporated by reference in this application.

FIELD OF THE INVENTION

The present invention relates to a system for inspecting and removing pellet-shaped articles (e.g., tablets) from a conveyer apparatus based on predetermined criteria.

BACKGROUND OF THE INVENTION

Processing of tablets, such as inspecting, marking, and/or laser drilling of tablets, is known in the art. Inspection units are typically configured to inspect and remove tablets from a conveyer mechanism that have been improperly processed in a previous processing operation. Previous processing operations may include marking the tablets with indicia, coloring the tablets, laser drilling holes in the tablets, and/or coating the tablets. These processing operations are typically completed upstream from the inspection unit such that the inspection unit may inspect if these processes have been properly completed.

It is important for the manufacturer to carefully inspect the pellet-shaped articles for defects, such as an improperly printed or coated side of the article, before the pellet-shaped article is distributed to the consumer so as to ensure the quality of the product and hence protect the safety of the consumer. Moreover, such defective articles must be separated from the acceptable articles based on the inspection results.

SUMMARY OF THE INVENTION

An aspect of the present invention relates to a conveyer apparatus including a plurality of carrier bars. Each carrier bar is structured to convey a plurality of pellet-shaped articles along a predetermined path. The conveyer apparatus may include one or more of the following aspects. For example, the conveyer apparatus may include at least one camera unit configured to sense a predetermined characteristic of the plurality of pellet-shaped articles. The conveyer apparatus may include a removal unit (e.g., downstream from the at least one camera unit) structured to remove at least a selected one of the plurality of pellet-shaped articles from at least a selected one of the plurality of carrier bars depending on whether the predetermined characteristic is sensed by the at least one camera unit. The conveyer apparatus may include a controller in communication with the at least one camera unit and the removal unit, the controller providing a signal to the removal unit in accordance with the predetermined characteristic sensed by the at least one camera unit. The removal unit may include a rotatable ejection drum having a plurality of extended vacuum nozzles along its length that is equal to the number of articles conveyed in each carrier bar. Each vacuum nozzle may be structured to selectively remove the article from the carrier bar by suction. Each camera unit may be configured to sense a plurality articles simultaneously. The predetermined characteristic may include at least one of marking error, printing misregistration, particular indicia, color, gel coating, and/or laser drilled hole. The conveyer apparatus may include a light assembly provided to the camera units to illuminate the articles as they are being sensed. The light assembly may include a dome structure and one or more LED lights. The dome structure may include a reflective interior surface adapted to reflect light from the LED lights onto the articles being sensed. The removal unit may selectively remove articles from the carrier bar by suction which are acceptable and passively allows rejected ones of the articles to be removed from the carrier bar. The removal unit may include a plurality of controllable valves associated with respective vacuum nozzles. Each of the valves may be selectively controlled by the controller to control vacuum pressure to the associated nozzle. Each vacuum nozzle may include a flexible tip portion adapted to engage the article. The ejection drum may be releasably mounted to allow removal for servicing, cleaning, and/or replacement to a drum having a different number and/or arrangement of vacuum nozzles. The at least one camera unit may include first and second camera units each configured to sense a predetermined characteristic of the plurality of pellet-shaped articles. The vacuum nozzles may be structured to remove all of the articles from the carrier bar by suction and selectively release suction applied to all of the articles to release the articles into either one of an accept bin or a reject bin depending on the predetermined characteristic sensed by the camera units. The ejection drum may hold articles for a longer distance and/or period of time depending on the predetermined characteristic sensed by the camera units. The ejection drum may hold acceptable articles for a longer distance and/or period of time than rejected articles. The camera units may sense both sides of each article for the predetermined characteristic, and one side of each article may be sensed before picking up by the removal unit and the other side of each article may be sensed after picking up by the removal unit.

Another aspect of the present invention relates to an inspection system that is configured for use with a conveyer apparatus including a plurality of carrier bars. Each carrier bar is structured to convey a plurality of pellet-shaped articles along a predetermined path. The inspection system includes at least one camera unit configured to sense a predetermined characteristic of the plurality of pellet-shaped articles, a removal unit, and a controller. The removal unit, downstream from the at least one camera unit, is structured to remove at least a selected one of the plurality of pellet-shaped articles from at least a selected one of the plurality of carrier bars depending on whether the predetermined characteristic is sensed by the at least one camera unit. The controller is in communication with the at least one camera unit and the removal unit. The controller provides a signal to the removal unit in accordance with the predetermined characteristic sensed by the at least one camera unit. The removal unit includes a rotatable ejection drum having a plurality of extended vacuum nozzles along its length that is equal to the number of articles conveyed in each carrier bar. Each vacuum nozzle is structured to selectively remove the article from the carrier bar by suction.

Another aspect of the present invention relates to an inspection system configured for use with a conveyer apparatus including a plurality of carrier bars. Each carrier bar is structured to convey a plurality of pellet-shaped articles along a predetermined path. The inspection system includes first and second camera units each configured to sense a predetermined characteristic of the plurality of pellet-shaped articles, a removal unit structured to remove the plurality of pellet-shaped articles from the plurality of carrier bars, and a controller in communication with the camera units and the removal unit. The controller provides a signal to the removal unit in accordance with the predetermined characteristic sensed by the camera units. The removal unit includes a rotatable ejection drum having a plurality of vacuum nozzles along its length that is equal to the number of articles conveyed in each carrier bar. The vacuum nozzles are structured to remove all of the articles from the carrier bar by suction and selectively release suction applied to all of the articles to release the articles into either one of an accept bin or a reject bin depending on the predetermined characteristic sensed by the camera units.

Another aspect of the present invention relates to a method for inspecting a predetermined characteristic of a pellet shaped article. The method includes conveying at least one row of articles along a predetermined path, picking up all articles from the predetermined path by suction, sensing all articles for the predetermined characteristic, and selectively releasing suction applied to the articles to directly deposit the articles into either one of an accept bin or a reject bin depending on whether the predetermined characteristic is sensed.

Another aspect of the present invention relates to an inspection system configured for use with a conveyer apparatus including a plurality of carrier bars. Each carrier bar is structured to convey a plurality of pellet-shaped articles along a predetermined path. The inspection system includes a removal unit structured to remove all the articles from the plurality of carrier bars by suction. The removal unit is configured to selectively release suction applied to the articles to directly deposit the articles into either one of an accept bin or a reject bin depending on whether either side of the article is defective.

Still another aspect of the present invention relates to process or print error traceability. Defects or other errors may be detected. One or more components of the apparatus may be associated with the defect or error, e.g., based on a positional relationship and/or time as to where and when the defect or other error occurred. For instance, certain example embodiments may track the area in the carrier bar from which a defect product is removed. That area may have a corresponding location in the printing or other upstream component. The area on a design or transfer roll in a printing application, for instance, may be further specified with reference to the time at which the error occurred. A count of errors for particular locations may be maintained and displayed to the user, e.g., in a matrix type layout corresponding to the carrier bar and/or other layout of the apparatus in certain example embodiments. Errors may be logged, and/or reports may be generated (potentially automatically) if the number of errors exceeds a predetermined threshold. The threshold values may be determined with reference to a particular area in the matrix, whether that area be a single pocket of an individual roll bar, a row of pockets or a column of carrier bars, a cluster, etc.

Still another aspect of the present invention relates to techniques for identifying the origin of a detected area on a carrier medium along a processing path.

Still another aspect of the present invention relates to an interface having a grid-like display to illuminate where errors have been detected. In this way, potential problems may be identified.

Still another aspect of the present invention relates to the provision of multiple smart cameras or multiple sets of smart cameras. The detection of errors may be distributed to the individual cameras and/or the individual sets of cameras, e.g., if they are provided with respective processors. In some forms, one set of cameras may be responsible for detecting coarse or larger defects or errors, whereas a second set of cameras may be responsible for detecting finer defects or errors. Color and/or black and white or grayscale cameras may be provided to serve these and/or other functions. Smart cameras may be scalable and in some cases may reduce (and sometimes even completely eliminate) the need to transfer raw or processed image data. For instance, in some forms of the invention, the only data that may be transmitted from a smart camera may be an indication as to whether there is a detected error or defect that should be tracked and/or addressed (e.g., through product removal). The number of each type of camera may vary and need not be the same. They may be provided in a ratio relative to one another and/or to the size of the carrier bar transporting the product thereunder. The cameras may be positioned in subsequent stages. Where the same numbers of cameras are provided in each stage, they may be substantially in-line or staggered. Where different numbers of cameras are provided, they may be staggered, centered relative to one another, or provided in some other relative position. Some overlap as between adjacent cameras in a stage may be desirable, e.g., for increasing accuracy and/or ensuring adequate coverage. A visual detection system of this or other sort may be provided or retrofitted to an apparatus in certain situations.

Still another aspect of the present invention relates to an ejection system that selectively removes products identified as being defective, damaged, or otherwise inappropriate, and/or that may be provided or retrofitted to an apparatus in certain situations. The ejection system may involve vacuum removal techniques as discussed herein.

Still another aspect of the present invention relates to an improved user interface. The user interface may facilitate changeover as between different predefined or custom defined recipes, e.g., for different products. The user interface may adjust relevant software settings, e.g., for different hardware configurations. The user interface may help keep track of metrics regarding product acceptance, rejection, yields, etc., e.g., on a camera-by-camera basis, on a type of camera by type of camera basis, on a carrier-by-carrier-basis, etc. These metrics may be visualized together with, or separate from, a matrix of where the errors have been detected in certain implementations.

Still another aspect of the present invention relates to a trainable visual detection system. The visual detection system may be trained against a product known to be acceptable. Pattern recognition may be performed as to the "master" product, and subsequent scans may be compared against this "master." Tolerances also may be set as to the degree of pattern matching required for an acceptable product or a degree of errors at which products should be removed. Such tolerances may vary based on a particular recipe, product, legal or other standard or guideline, etc.

Still another aspect of the present invention relates to hardware changeover enabled by carrier bar replacement, vacuum shoe/drum replacement, camera addition/subtraction/repositioning, etc.

One feature of certain forms of the invention relates to the ability to accommodate fast product handling from the inlet hopper to the carrier bars, and through the equipment. As will be appreciated, the actual production rate is a function of product size, shape, and lubricity. However, in certain examples, the product handling through this stretch of the apparatus may be at a rate of 250,000 to 400,000 tablets per hour, with a low (and sometimes no) amount of product being damaged through the process.

Another feature of certain forms of the invention relates to a color vision or imaging system configured to differentiate between different colors of products, e.g., to help avoid, and stop production in the event of, cross contamination, to weed out defective products, etc.

Another feature of certain forms of the invention relates to a high resolution vision or imaging system that inspects the product to help ensure that print quality is legible and correctly aligned on the product. Confirmation may be made by an integrated vision system, suitable in some examples for rejecting 99% or higher of non-passable product based on individual characters with an accuracy of at least 95%. The system may in some examples reject at least 99.9% of tablets with major defects.

Another feature of certain forms of the invention relates to an apparatus having a configuration such that product that does not pass the visual inspection test will be considered rejected and be segregated from acceptable product.

Another feature of certain forms of the invention relates to the ability to log and record data at runtime, with the logs being stored as batch or individual reports that are retrievable by a user/operator.

Another feature of certain forms of the invention relates to the ability to produce high quality printed product at production rates with a reduced amount of operator interface required during use.

Still another feature of certain forms of the invention relates to the ability to detect problems that occur when the ink does not fully adhere to a product, when coatings on products flake off (e.g., contaminating the ink), indistinct markings are made, the incorrect products are improperly introduced into the batch, etc.

Still another feature of certain forms of the invention relates to color inspection techniques for products.

Still another feature of certain forms of the invention relates to an improved user interface that facilitates software and/or hardware changeover, makes it possible to diagnose problems by tracking where and/or when in the apparatus problems are noticed and thus likely to have occurred, enables compliance with relevant regulations based on functional certification, and/or the like.

Still another feature of certain forms of the invention relates to one or more groups of one or more cameras. Such cameras in some forms of the invention may be "smart" cameras having processors collocated with them, allowing for distributed processing that potentially increases throughput with the addition of new modules.

Still another feature of certain forms of the invention relates to printer error traceability, through which it is possible to reduce printing and/or other processing errors by identifying the source of the error (e.g., a flat spot on a design roll, etc.).

Still another feature of certain forms of the invention relates to an adjustable and/or removable vacuum drum, optionally having retractable bearings.

Still another feature of certain forms of the invention relates to an ejection manifold.

Still another feature of certain forms of the invention relates to the presence of a retrofittable vision and/or ejection system.

Still another feature of certain forms of the invention relates to simplified changer over, involving a vacuum shoe, vacuum drum bars, and product/carrier bar conversion. In certain forms of the invention, these hardware components may be changed over with the aid of a user interface that helps account for these and/or other changes. For instance, the software may help plan for more or fewer row bars, different numbers of pockets in the different row bars, etc.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 8 is an exploded view of the ejection drum, vacuum shoe, and vacuum manifold including solenoid pack of the inspection system of FIG. 5;

FIG. 9 is a perspective view of the ejection drum, vacuum shoe, and vacuum manifold of FIG. 8;

FIG. 11 is a side view of the vacuum shoe of FIG. 8;

FIG. 12 is a cross-sectional view through line 12-12 of FIG. 11;

FIG. 13 is an end view of the vacuum shoe of FIG. 11;

FIGS. 17 and 18 are perspective views of a dome structure for a light assembly according to an embodiment of the invention;

FIG. 19 is a cross-sectional view of a nozzle for an ejection drum according to an embodiment of the invention;

FIGS. 20-1 to 20-4 are schematic views showing the releasable mounting of the ejection drum according to embodiments of the invention;

FIG. 26 is an example operation screen that may be displayed to a user/operator in accordance with an example embodiment;

FIG. 27 is an example operation screen that includes overall equipment effectiveness (OEE) performance monitoring in accordance with an example embodiment;

FIG. 28 is an example design roll data matrix screen in accordance with an example embodiment;

FIGS. 31 and 32 are example user maintenance screens in accordance with an example embodiment; and FIG. 33 is an example automatic vision system calibration verification screen in accordance with an example embodiment.

DETAILED DESCRIPTION OF ILLUSTRATED EMBODIMENTS

Figure 1:
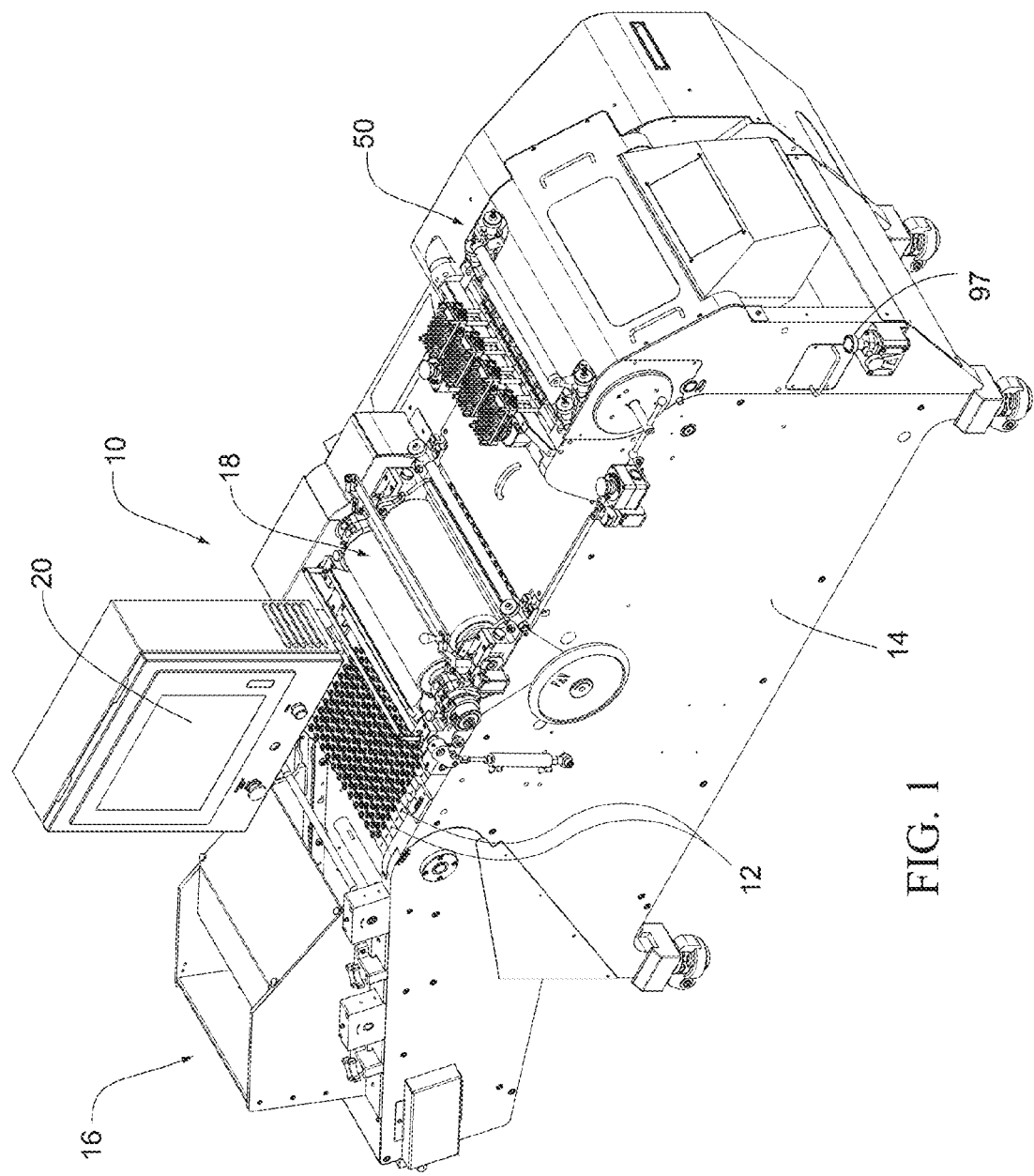
FIG. 1 is a perspective view of a conveyer apparatus including an inspection system according to an embodiment of the invention.
Figure 2:
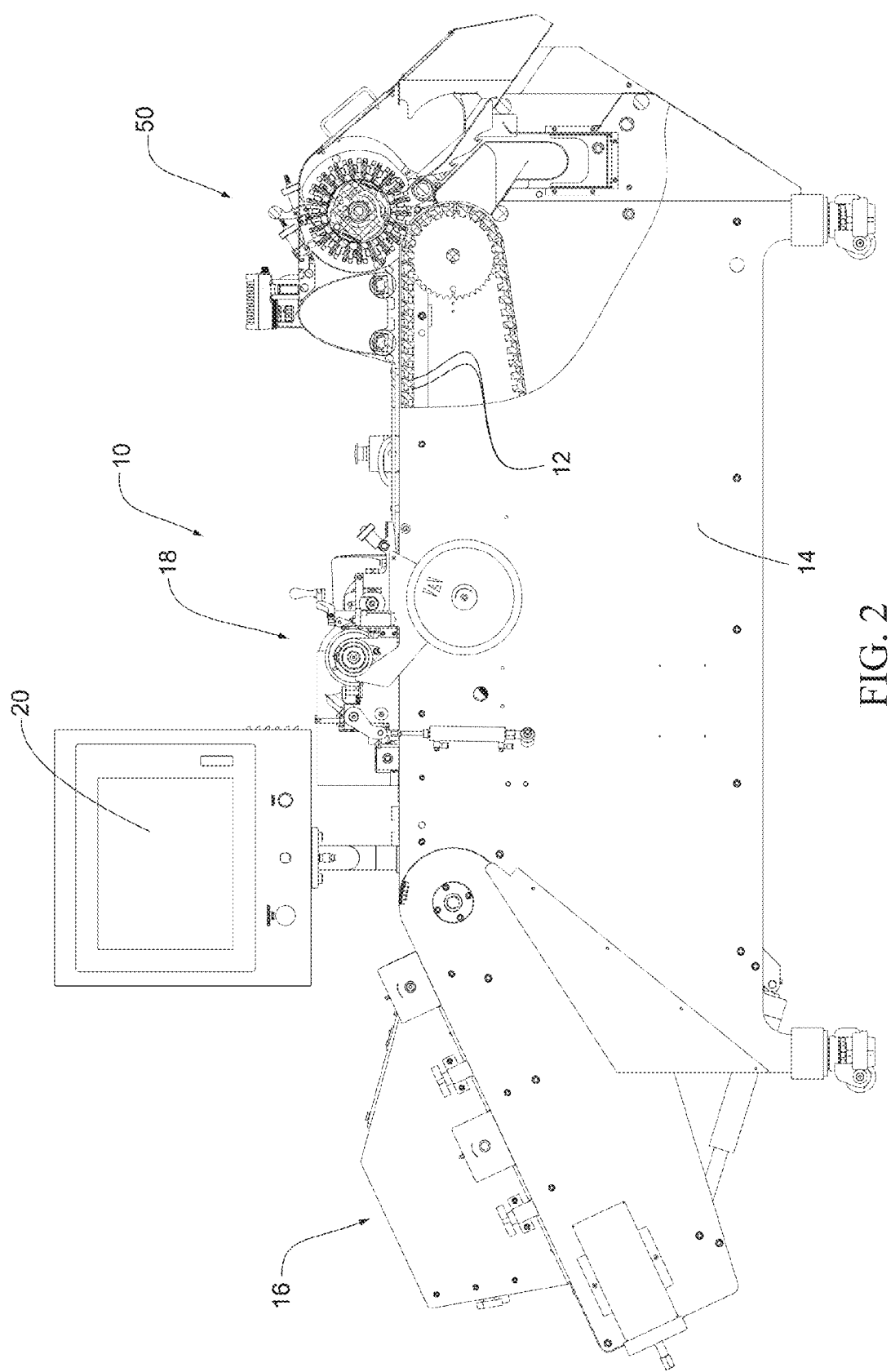
FIG. 2 is a side view of the conveyer apparatus of FIG. 1, with a portion of the apparatus shown in cross-section.
Figure 3:
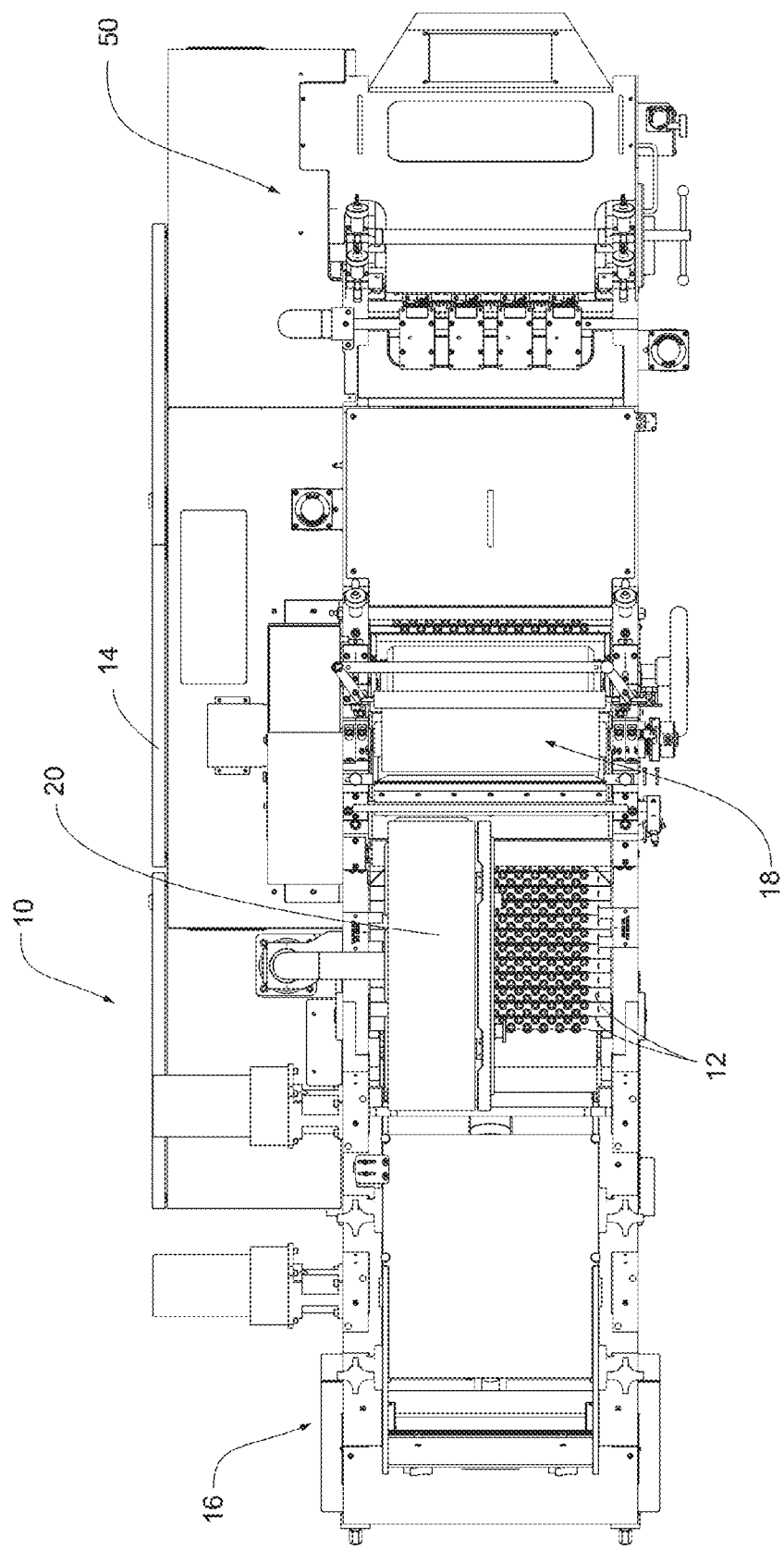
FIG. 3 is a top view of the conveyer apparatus of FIG. 1.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

Certain forms of the invention relate to a variable ramp printer, including an offset printer with automatic print quality vision inspection and/or defective product removal. Thus, certain forms of the invention are configured to produce high-quality printed product at production rates with a reduced amount of operator interface and maintenance. Safety devices may be built into the system, e.g., to help ensure safe operation and maintenance by trained personnel.

As an overview of certain example techniques, it is noted that the variable ramp printer may operate by placing product into an inlet hopper located at a ramp section of the system. Carrier bar pockets are custom designed to work with a specific ramp feed angle determined through testing. The product therefore may be gravity-fed from the inlet hopper to the carrier bar pockets, where it is properly oriented and conveyed past rotating brushes, designed to provide an increased carrier bar fill rate, while also reducing the likelihood of stray product from exiting the hopper. The product is transported through the print unit, where the engraved design roller transfers ink to the offset roller, which then transfers the logo on to the product. The product is conveyed along an ink drying section, where color cameras verify the tablet color. Non-conforming product is gravity discharged off the front of the conveyor, assisted by a discharge blow-tube. Following the color inspection, a row of grayscale cameras captures high-resolution images of the product surface and the printed logo. The image is analyzed by the vision system to determine if the printed logo meets the quality standard defined by a pre-trained reference logo image (e.g., a pre-trained golden reference logo image). If the printed logo quality passes this first test, the position of the logo on the tablet is inspected to verify that it is centered within a pre-set tolerance. Other visible features and/or blemishes in the captured image may also be inspected so as to help identify and/or capture, for example, broken products, coating defects, etc. The results of the inspections are entered into the product tracking system, which stores an accept, reject or empty-pocket result for each carrier bar pocket location along the conveyor. A time or other index may be associated with each row bar. Non-conforming product is gravity discharged off the front of the conveyor, assisted by a discharge blow-tube. Product that is determined to be acceptable by the automatic vision inspection system is lifted out of the carrier bar pockets using soft, silicone vacuum suction cups rotating around a synchronized product eject transfer drum. The accepted product is transferred from the eject drum to the discharge chute where it exits the machine. As will be appreciated, the example process steps may be performed in any suitable order.

It is noted that the printing, conveyor, inspection, ejection, and/or other systems may be provided in any suitable combination or sub-combination. Furthermore, various "sub-aspects" of the visual inspection system also may be provided in various combinations and sub-combinations. For instance, the color and grayscale imaging techniques may be provided together or separately. Furthermore, certain functions described above as involving color cameras may be performed with grayscale cameras, and vice versa. The imaging techniques may also be provided as a part of a retrofit package that may be added to existing conveyor or other type systems.

Although certain example embodiments have been described as including a ramp type printer, a flat or more flat type system also may be used in connection with different embodiments of this invention. In other words, ramping and/or gravity fed techniques are not necessarily required by all embodiments.

FIGS. 1-4 illustrate a conveyer apparatus 10 including a plurality of carrier bars 12 structured to transport or convey a plurality of pellet-shaped articles along a predetermined conveyer path. It should be appreciated that the carrier bars may be adapted for use with any suitable pellet-shaped article, e.g., tablets, capsules, pills, etc.

The apparatus may be a ramp-type conveyer including incline, horizontal, and decline portions as disclosed in U.S. Pat. No. 5,655,453, which is incorporated by reference in its entirety. The conveyer path represents the direction of travel of the carrier bars.

The conveyer apparatus 10 is supported upon a frame 14 having spaced legs for providing a free-standing support. The frame is also structured to support a feed hopper 16, a marking apparatus 18, an inspection system 50, and a display monitor 20 that displays diagnostic information to an operator.

In certain examples, the frame may include various sections or components for supporting the system in whole or in part. A flat bed section may provide support for the overall system and allow mounting for print and inspection systems. A ramp section may include an adjustable, angled ramp feed system that is designed to increase the carrier bar pocket fill rate. The product infeed hopper may be located on the ramp section of the frame. A DC linear actuator motor may be provided to help move the ramp section up and down. The infeed hopper assembly may be used to transfer the product into the carrier bar pockets. The hopper level may be properly maintained to reduce the likelihood of damage to the product and achieve the desired increased carrier bar pocket fill rate. Leveling Casters may be mounted on the bottom of the base frame assembly to allow portability and to provide the ability to level the system. An operator control panel may be mounted to the base frame assembly to allow an operator to interface with the variable angle ramp print system. A handwheel may be used to move the product carrier bars in the forward direction, e.g., when there is no power to the motors.

In the illustrated embodiment, each of the carrier bars includes one or more article receiving pockets disposed transversely along their length. The pockets of the carrier bars operate to receive and entrain articles from the feed hopper 16, and move the articles along the conveyer path. The feed hopper may be provided along an incline portion of the conveyer. In other words, tablets may be conveyed through the system using carrier bars with machined pockets, custom designed for the product to be imprinted. The carrier bars may be spaced apart along the conveyor, e.g., at regular intervals (for example, 1" intervals). The carrier bars may be designed for ease of changeover, e.g., incorporating "snap-off" removal and/or "press-on" insertion features. In an example product feed system, a variable speed carrier bar conveyor system may utilize precise servo motor position control. The conveyor servo motor may be arranged along the main axis of the machine, and the print unit servo motor may be electronically geared to this axis.

A primary hopper brush may help ensure that only properly oriented tablets are conveyed through the system. The brush rotational speed may be controlled from via a user interface. The primary hopper brush may be an upper one of two large brushes. A secondary hopper brush, by contrast, may be used to agitate the product and assist product feeding into the carrier bar pockets. The brush rotational speed for the secondary hopper brush also may be controlled via the user interface, and the secondary hopper brush may be the lower of the two hopper brushes. A laydown brush may help ensure that the product is properly seated in the carrier bar pockets and also may help reduce the likelihood that tablets that are outside of the carrier bar pockets enter the imprinting area. A bar vibrator, located under the carrier bars in the flat-bed area just before the lay down brush, may help ensure that the product is properly seated in the carrier bar pockets. The hopper blowback tube contains of a set of air nozzles designed to remove product from the carrier bar pockets before they exit the hopper. When the stop button is pressed, the hopper blowback nozzles are activated to restrain the product within the hopper while the conveyor system continues to run for a set distance until the carrier bars have been cleared of product.

The carrier bars are conveyed past the marking apparatus 18 for marking desired indicia onto the articles. In the illustrated embodiment, the marking apparatus 18 includes a design roll that forms the indicia to be applied to the articles, and which is disposed within an appropriate supply of ink (not shown), and a printing roll which is in contact with both the design roll and the articles which are to receive the indicia, for transferring the ink-laden indicia from the design roll to the articles in question. However, it is contemplated that the marking apparatus may be an ink jet.

If an offset printer is used, it may have the following example structure. A metal design roller, engraved with the logo designs, may rotate within an ink pan. Ink in the pan fills the engravings. The design roller may in some cases be referred to as a rotogravure cylinder. A doctor blade may wipe the excess ink from the design roller back into the pan. A rubber offset roller may contact the design roller, pick up the ink from the design roller etches, and transfer the ink to the product surface. As alluded to above, an ink pan may hold the ink for the design roller. As the design roller rotates, the mixing action may help maintain the consistency of the ink within the pan. An offset roller stripper plate may help reduce the likelihood of product sticking to the offset roller after printing. The stripper plate may be custom designed for the product to be printed. A print unit servo motor may be electronically geared to the conveyor for precise synchronization of the print unit relative to the carrier bars.

Following the marking apparatus, the carrier bars convey the articles past the inspection system 50 according to an embodiment of the invention. The inspection system is structured to inspect and remove specified pellet-shaped articles from the conveyor apparatus based on predetermined criteria.

In illustrated embodiment, the inspection system 50 includes a camera unit 60, a removal unit 70, and a controller 80. In use, each article A is inspected by the camera unit 60 for one or more particular criteria or characteristics (e.g., marking error, printing misregistration, etc.), and then brought past the removal unit 70 configured to remove acceptable articles that have met the particular characteristics as determined by the camera unit and eject the acceptable articles into an accepted product discharge chute or accept bin 90. Defective or flawed tablets that have not met the particular characteristics are allowed to pass by the removal unit and are discharged into a separate rejected product discharge chute or reject bin 92.

The camera unit 60 is provided along the conveyer path and is configured to sense a predetermined characteristic of the article. In the illustrated embodiment, the camera unit is configured to sense whether one side of the article has been properly marked. If the camera unit determines that a tablet-shaped article has been properly marked, then that particular article will be removed by the removal unit from the conveyer apparatus.

One or more camera units may be provided to conveyer apparatus, with each camera unit configured to sense a plurality of pockets simultaneously. Each camera unit may be configured to monitor any number of pockets provided in each of the carrier bars. For example, each camera unit may be dedicated to a certain area of the carrier bar and configured to monitor the pockets provided in such area of the carrier bar regardless of number of pockets. The fields of view of the camera units may overlap with one another to ensure that the entire carrier bar is monitored. The controller may be adjusted to set the number of pockets being monitored by each camera unit. In an exemplary embodiment, each camera unit may be configured to monitor an area including 2-8 pockets, e.g., 4 camera units provided to monitor carrier bar with 24 pockets with each camera unit configured to monitor 6 pockets.

Also, it should be appreciated that the camera unit may be configured to sense other predetermined characteristic of the article (e.g., particular indicia, color, gel coating, laser drilled holes, etc.). That is, other processing operations may precede the inspection system, and the inspection system may be configured to inspect the accuracy of such operations and remove articles accordingly.

A diffuse reflectance LED light assembly 62 is provided to the camera unit 60 to properly illuminate the respective side of the article as it is being sensed. For example, the light assembly 62 includes a dome structure 63 and one or more LED lights 64 provided along the lower edge of the dome structure. The light assembly provides an indirect lighting arrangement in which light from the LED lights is not directly focused onto the carrier bars, i.e., LED lights oriented away from the carrier bars and the dome structure reflects light onto the carrier bars and/or defines an illuminated area or lighted interior space. In an exemplary embodiment, the interior surface 63(1) of the dome structure 63 may include a reflective surface (e.g., white coating, e.g., paint or lacquer) adapted to reflect light from the LED lights 64 onto the carrier bars and the articles to be sensed. In an embodiment, each LED light is configured to intermittently emit light (e.g., strobe type lighting), with the light appropriately timed with inspection by the camera unit. One or more openings 66 are provided to the top of the dome structure 63 and aligned with a respective camera unit 60 to allow the camera unit to operate therethrough. Each camera unit may be adjustably mounted (e.g., slidably mounted for lateral or side-to-side movement) with respect to the conveyer apparatus for optimal performance.

FIGS. 17 and 18 show a dome structure 63 according to an embodiment of the invention. As illustrated, the dome structure is in the form of a single elongated dome with one elongated opening 66 that allows the one or more camera units to operate therethrough. In an alternative embodiment, the light assembly may provide individual domes for individual cameras.

However, alternative and/or additional arrangements may be provided to enhance lighting of the carrier bars and/or sensing of the articles by the camera unit. For example, the carrier bars may include a coating (e.g., white coating) to enhance the contrast between the article and the carrier bar, for improved inspection efficiency/results. In another example, the carrier bars may be constructed of a material (e.g., plastic material) so they are clear or transparent, which may allow sensing the bottom side of each article without removing the article from the carrier bar, i.e., camera unit able to sense through the thickness of the carrier bar. Since the top side will remain exposed, the entire article can be inspected with the article remaining in the same orientation.

The camera units provide signals to the controller 80, which signals the removal unit so that specified articles can be removed from the conveyer apparatus.

Another example vision inspection system may include the same or similar components functioning in the same of similar ways. For instance, one or more high resolution black and white or grayscale inspection cameras may be provided. In one form, four inspection cameras mounted adjacent to each other, spaced apart at regular intervals (e.g., 3.38" apart) and above the carrier bars. The number of and distance between adjacent cameras, as well as the height above the carrier bars, may be selected based in part on the length of the carrier bars, focal distance of the cameras, etc. For example, if the maximum printable area of a carrier bar is 13.75 inches and four cameras are provided, each camera may be responsible for inspecting a 3.75 inch area of the carrier bar. The field-of-view (FOV) of each camera may be made to overlap the FOV of the adjacent camera, providing the vision system with a full-view of the carrier bar. Each camera may be a "smart camera," e.g., in the sense that it may have a processor integrated therein. For instance, each camera may have a built-in 1 GHz processor, 64 MB Flash memory and 128 MB image processing memory. When a trigger is sent to the camera, it will acquire an image, inspect the product in the carrier bar pockets and send the results to a programmable logic controller (PLC). A color inspection system component may include one or more (e.g., two) color cameras mounted above the carrier bars, e.g., as described above and possibly in connection with the variables identified above. The color inspection system may be used to help avoid product cross contamination. Suitable color cameras include, for example, Cognex Insight 5400 cameras, although other camera types may be used in different embodiments. C-mount Megapixel lenses may be provided for the cameras in some implementations, although higher or lower resolution lenses also may be used in different embodiments.

Lighting connected to a strobe controller may be collocated with the color inspection system components or otherwise may be provided over the carrier bars. LED lighting may be advantageous in that it may provide high-intensity lighting. In certain embodiments, the LED lighting may be elongated high-intensity strobe white LED line lights for illumination. The LED lighting may be longer than the carrier bars. For instance, if the maximum printable area of a carrier bar is 13.75 inches, the LED line lights may be 18" long. In certain examples, more lighting may be provided for the black and white or grayscale cameras as compared to the color cameras. For instance, two LED line lights may be provided for the black and white or grayscale cameras, whereas one LED line light may be provided for the color cameras. A lighting controller may provide a signal to the LED lights for high-intensity strobe illumination. As indicated above, an inspection dome cover may provide for a bright, uniform "cloudy day" lighting effect for high contrast product quality inspection. Aspects of the strobe (e.g., timing between pulses, length of pulses, intensity, trigger source, etc.) may be programmed and/or controlled.

Figure 5:
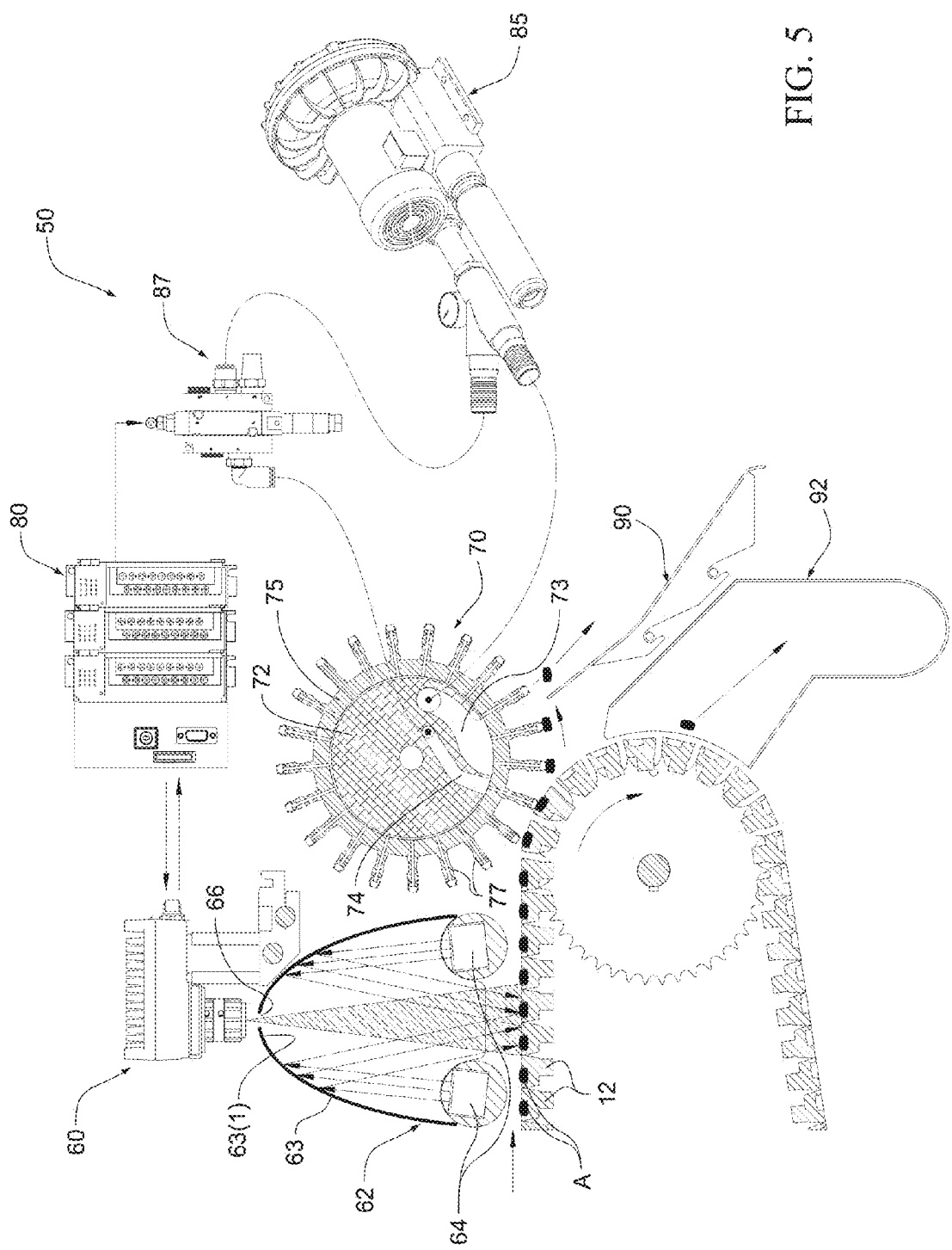
FIG. 5 is a schematic view of an inspection system according to an embodiment of the invention.

In the illustrated embodiment, as shown in FIG. 5, the removal unit 70 includes a stationary vacuum shoe 72 and a product ejection drum 75 rotatable with respect to the vacuum shoe. The vacuum shoe 72 includes a constant vacuum portion 73 communicated with a vacuum source 85, and a variable vacuum portion 74 communicated with the vacuum source via a controllable solenoid valve 87. The product ejection drum 75 includes a plurality of vacuum nozzles or suction cups 77 communicated with the vacuum shoe.

The product ejection drum is adjustably mounted to the frame of the conveyer apparatus to allow selective adjustment of the drum with respect to the carrier bars, i.e., drum is adjustable to adjust the distance between the nozzles and the carrier bars or articles. In addition, the vacuum shoe and the ejection drum are releasably mounted to the frame of the conveyer apparatus to allow easy removal of the shoe and drum from the conveyer apparatus, e.g., for servicing, cleaning, and/or changing shoe/drum to correspond with carrier bar pocket arrangement.

Figure 4:
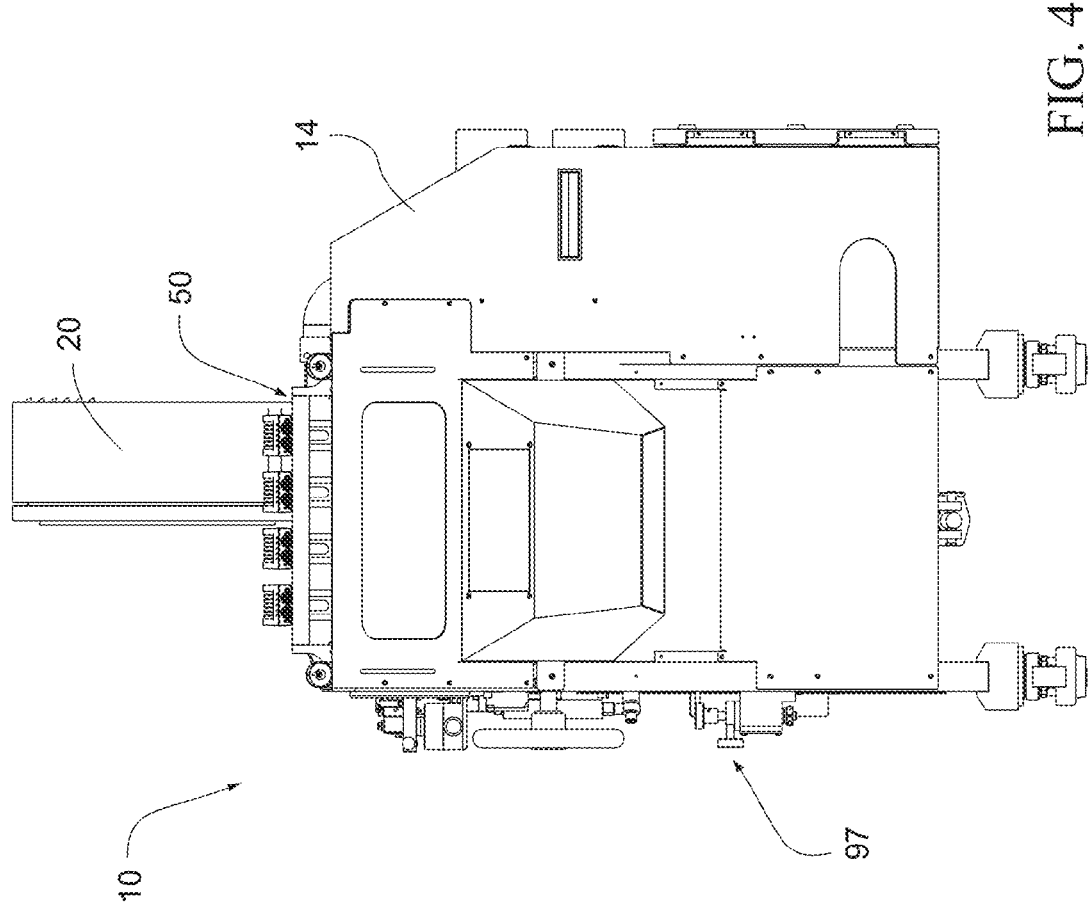
FIG. 4 is a front view of the conveyer apparatus of FIG. 1.
Figure 6:
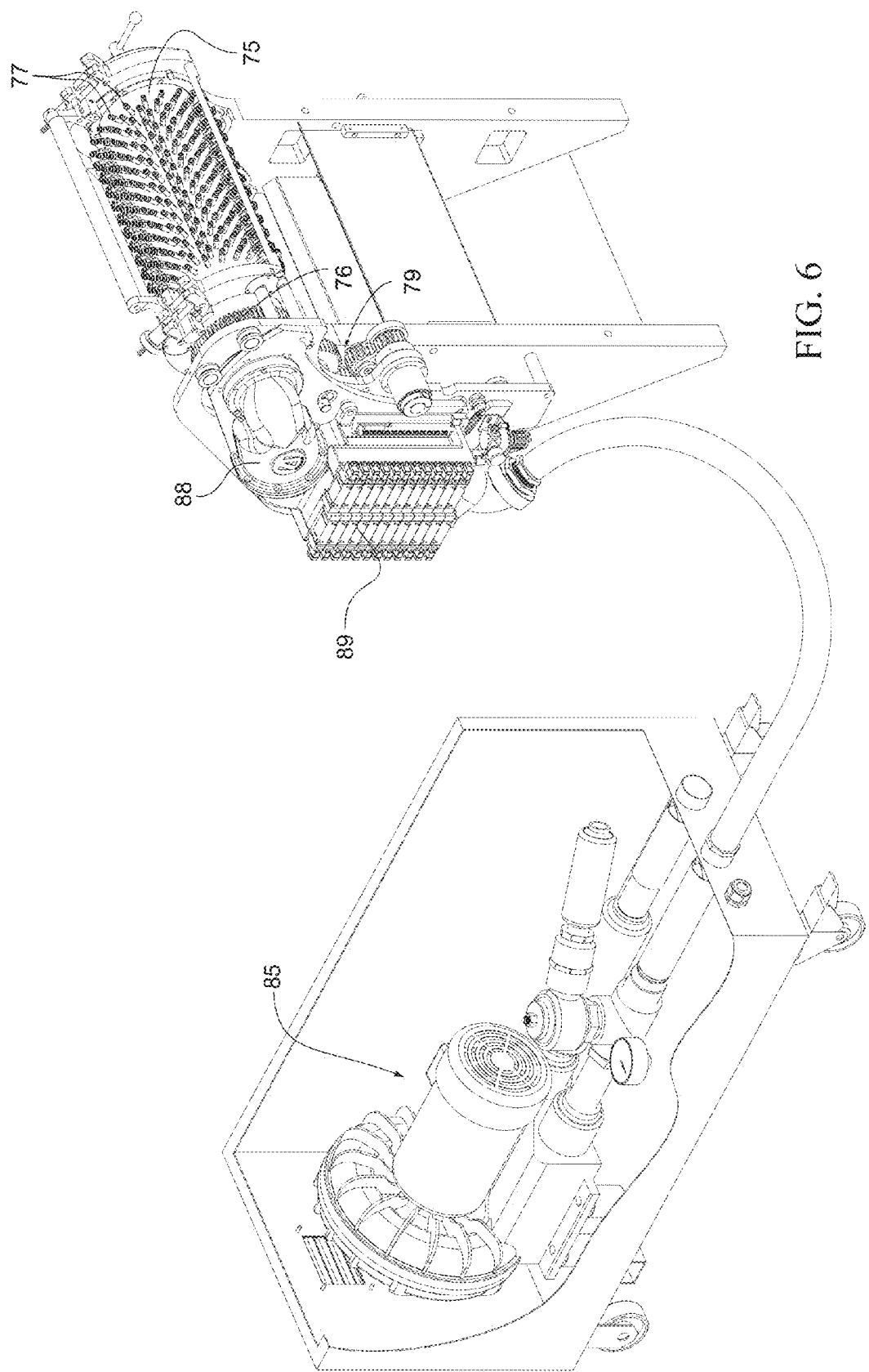
FIG. 6 is a perspective view of the inspection system of FIG. 5.
Figure 7:
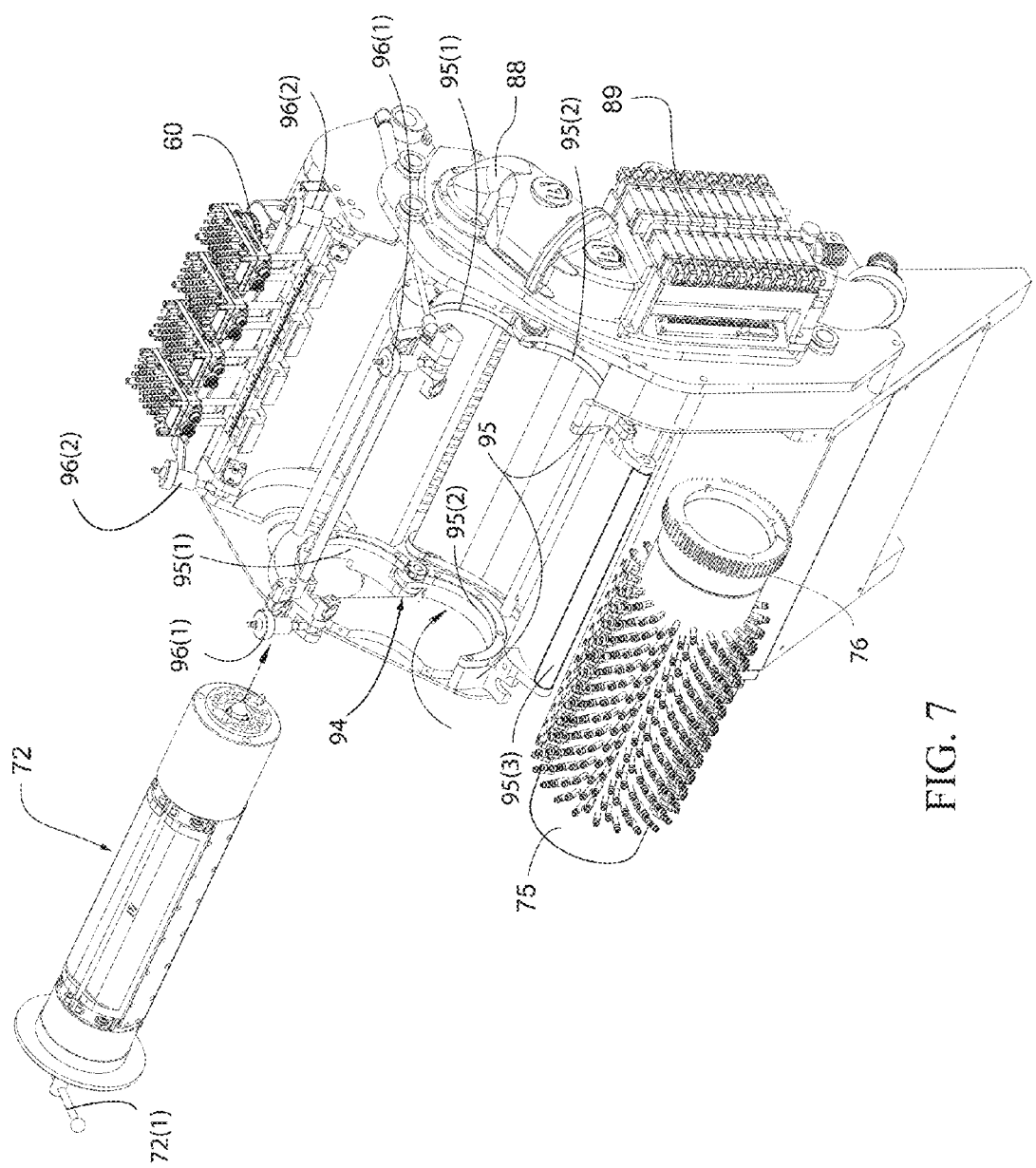
FIG. 7 is an exploded view of the inspection system of FIG. 5.
Figure 10:
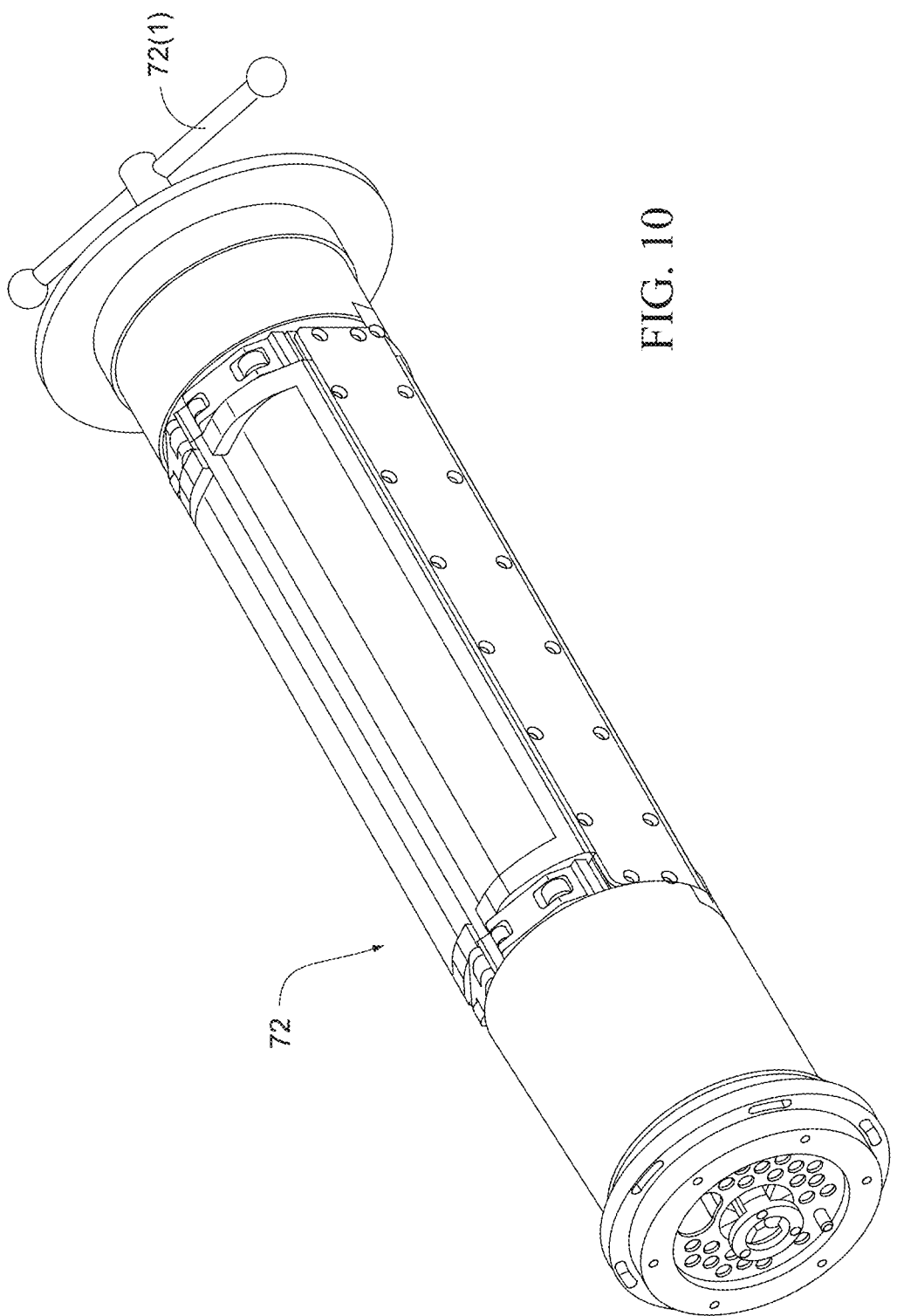
FIG. 10 is a perspective view of the vacuum shoe of FIG. 8.
Figure 14:
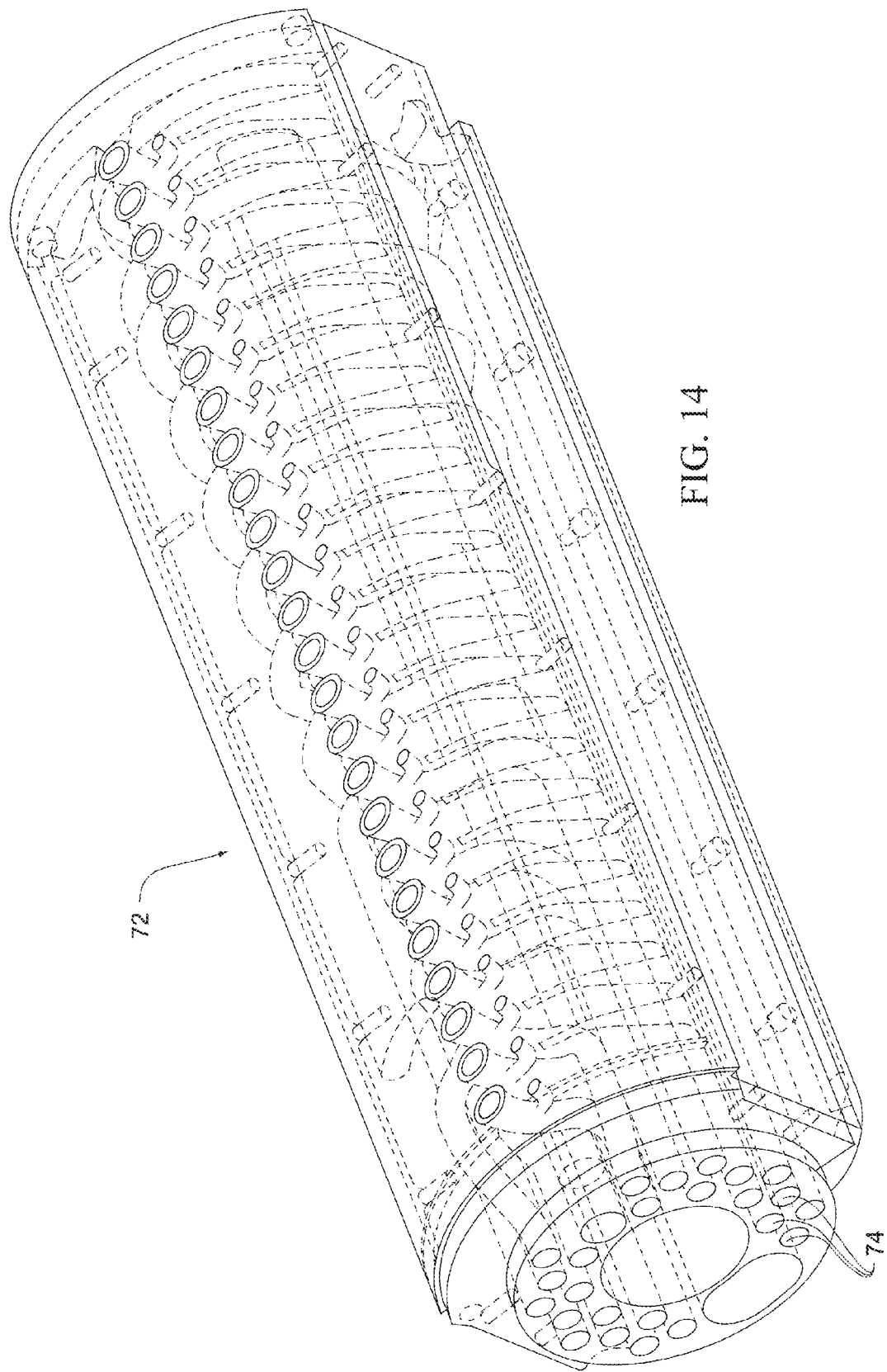
FIG. 14 is a perspective view of the vacuum shoe of FIG. 8.
Figure 15:
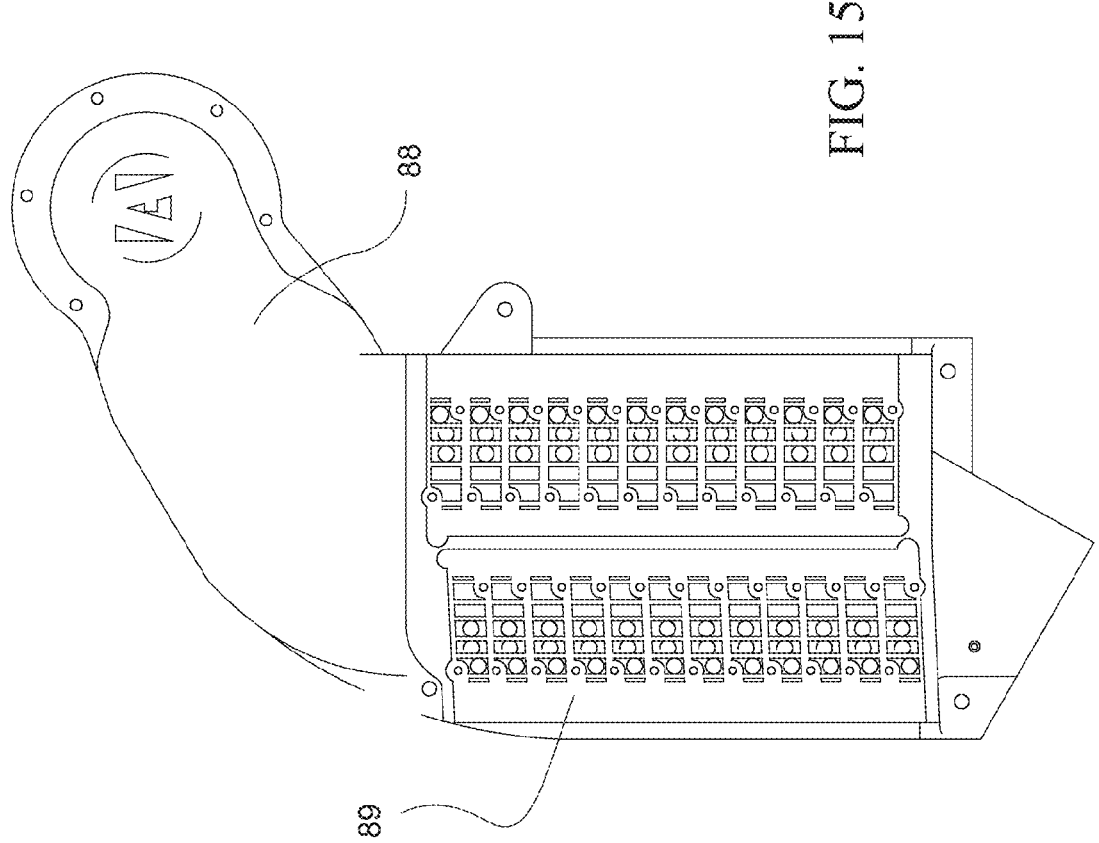
FIG. 15 is a side view of the vacuum manifold of FIG. 8.
Figure 16:
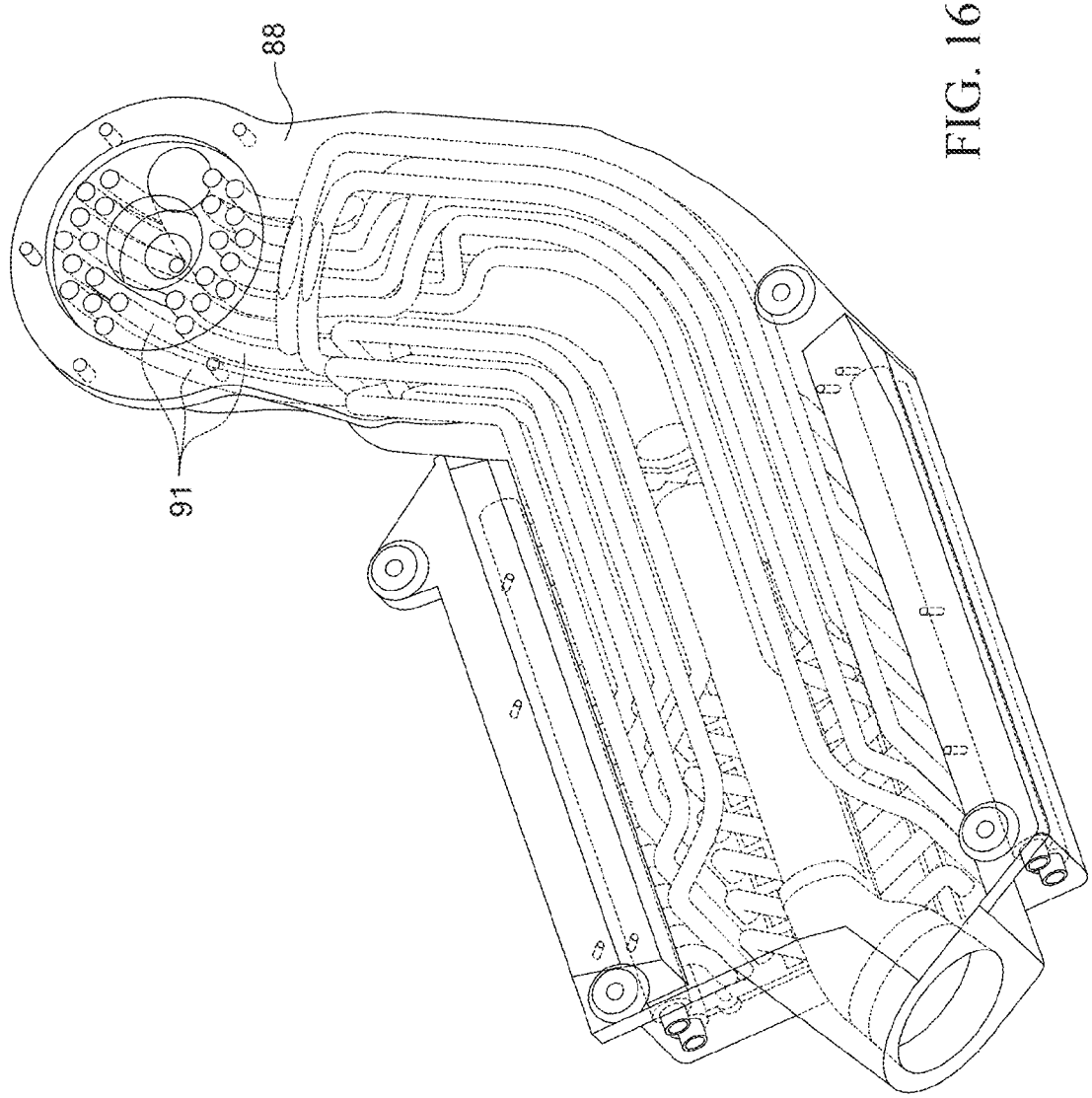
FIG. 16 is a perspective view of the vacuum manifold of FIG. 8.
Figures 4, 20:
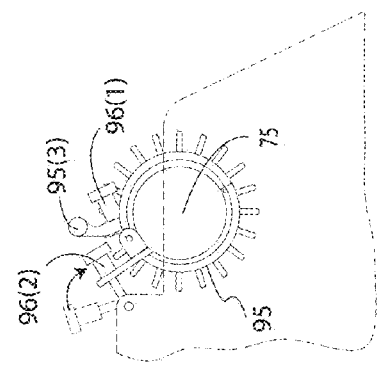
Figures 3, 20:
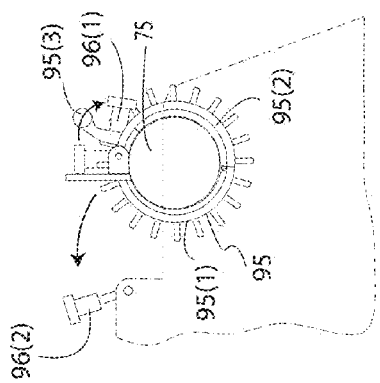
Figures 2, 20:
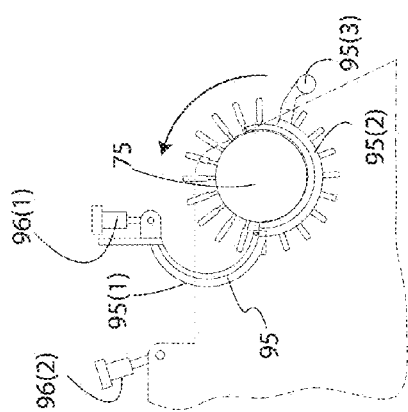
Figures 1, 20:
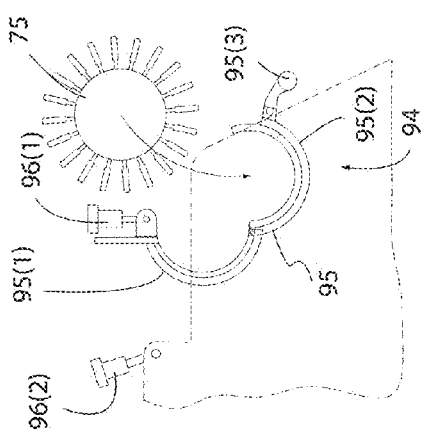

FIGS. 7 and 20-1 to 20-4 show the releasable mounting of the ejection drum 75 according to embodiments of the invention. As illustrated, a drum mount 94 is provided to the frame 14 to releasably secure the drum in an operative position. In the illustrated embodiment, the drum mount 94 includes a clamp-type arrangement with spaced apart clamp structures 95 structured to support respective ends of the drum. Each clamp structure 95 includes an upper arm 95(1) and a lower arm 95(2) pivotally mounted to the upper arm 95(1). In use, the ejection drum 75 is inserted into the spaced apart lower arms 95(2) (e.g., see FIGS. 7 and 20-1), and then the lower arms 95(2) are pivoted into engagement with respective upper arms 95(1) via the hand bar 95(3) (e.g., see FIG. 20-2) to secure the ejection drum within the drum mount (e.g., see FIG. 20-3). The upper and lower arms 95(1), 95(2) of each clamp structure are secured to one another by a locking pin 96(1) (e.g., see FIG. 7) which may be rotated between unlocked and locked positions (e.g., see FIG. 20-3). Once the ejection drum is secured within the drum mount, the drum mount 94 is pivoted via the hand bar 95(3) into an operative position with respect to the carrier bars as shown in FIG. 20-4. The drum mount 94 is secured in the operative position by locking pins 96(2) (e.g., see FIG. 7) which may be rotated between unlocked and locked positions (e.g., see FIG. 20-4). Movement of the drum mount 94 into the operative position also moves the gear teeth 76 on one end of the ejection drum into engagement with the gear assembly 79 structured to rotate the ejection drum in use (e.g., see FIG. 6). One or more adjustment knobs (e.g., see adjustment knob 97 in FIGS. 1 and 4) may be provided to adjust the position of the drum mount and hence the ejection drum with respect to the carrier bars, e.g., selectively adjust the distance between the nozzles of the ejection drum and the carrier bars. Once the drum mount and ejection drum are in the operative position, the vacuum shoe 72 may be inserted into the interior of the ejection drum 75 and releasably locked in position, e.g., via the lock handle 72(1) provided on one end of the vacuum shoe as shown in FIGS. 7 and 10 for example.

The drum 75 includes multiple sets of nozzles 77 arranged along a length or axis of the drum, and each set of nozzles matches the number and arrangement of pockets in each carrier bar. In an exemplary embodiment, each carrier bar includes 24 pockets separated into two staggered rows of 12 pockets. Accordingly, the drum provides multiple sets of nozzles separated into groups of 24, with each nozzle associated with a respective pocket. However, it should be appreciated that other suitable numbers of pockets may be provided to each carrier bar, and hence other suitable numbers of nozzles.

As a result, one or more specified articles from each carrier bar may be removed from their respective pocket as it passes by the removal unit by selectively controlling a set of nozzles. That is, each nozzle from the set is associated with a single pocket in each carrier bar, and each nozzle may be selectively activated to permit or prevent vacuum air from the vacuum shoe to be applied therethrough, therefore selected articles from the carrier bar may be selectively removed or picked up by the nozzles depending on whether the articles are determined to be "acceptable" or "defective" by the camera unit as described below.

If an article is determined to be "acceptable", the controller 80 signals the solenoid valve 87 to permit vacuum air to be applied to the selected variable vacuum portion 74 associated with the selected nozzle 77, which allows the selected nozzle to remove (e.g., by suction) the individual article from that pocket in the carrier bar. As the drum 75 continues to rotate relative to the vacuum shoe 72, the nozzle will move from communication with the associated variable vacuum portion 74 to the constant vacuum portion 73 which will continue to retain the article with the nozzle. Further rotation of the drum will move the nozzle out of communication with the constant vacuum portion and allow the article to eject or fall into the accepted product discharge chute 90.

If an article is determined to be "defective", the controller 80 signals the solenoid valve 87 to prevent vacuum air to be applied to the selected variable vacuum portion 74 of the selected nozzle 77. As a result, the defective article is allowed to pass by the respective nozzle of the drum and is discharged or falls into the rejected product discharge chute 92.

FIGS. 6-16 show various views of the vacuum shoe 72, the ejection drum 75, the vacuum source 85, and the vacuum manifold 88 including solenoid pack 89 associated with the solenoid valve. The solenoid pack 89 includes one or more solenoids to match the number of valves associated with the axially spaced nozzles in the drum and hence the number of pockets in each carrier bar. Each solenoid may be selectively controlled to control the valve and hence vacuum pressure to the associated nozzle. Also, each solenoid is associated with a solenoid tube 91 (e.g., see FIG. 16), each tube 91 being communicated with the respective tube or variable vacuum portion 74 in the vacuum shoe 72 (e.g., see FIG. 14). The drum rotates relative to the shoe as the carrier bars are conveyed along the conveyor path. As the carrier bars pass below the drum, a set of nozzles along the length of the drum align with respective pockets of each carrier bar. If the articles within the pockets are determined to be acceptable, then the solenoid associated with the nozzle aligned with such article is activated, e.g., to remove the article by suction from the pocket and release into the discharge chute for acceptable articles. For any articles that are not acceptable, the solenoid is not activated and the article continues with the carrier bar until gravity allows the article to be released into the discharge chute for defective articles. In this embodiment, all articles (including acceptable tablets) are ejected in the event of solenoid failure.

As best shown in FIG. 19, each nozzle 77 includes a base portion 77(1) extending from the drum 75 and a tip portion or article engaging portion 77(2) provided to the free end of the base portion. The base portion 77(1) defines a passage 77(3) for communicating vacuum pressure therethrough. In the illustrated embodiment, the tip portion 77(2) includes a gusseted or bellows configuration with one or more bendable portions 77(4) to add flexibility to the tip portion. The gusseted configuration is structured to cushion impact with the article in use, maximize compliance by allowing article differentiation and misalignment, and/or maximize vacuum pressure in use. In an embodiment, the tip portion (e.g., constructed of a more flexible material than the base portion, e.g., such as silicon) may be formed separately from the base portion and attached thereto. However, the nozzle may include other suitable structures and may be constructed of other suitable materials to enhance engagement with the article.

The ejection system change parts for a particular product may include a vacuum shoe and an eject drum. As explained in detail above, The vacuum shoe helps channel the vacuum from the machine-mounted vacuum valves to the corresponding row of carrier bar pockets, and the eject drum consists of a hollow cylinder with rows of suction cups mounted to stems around the circumference of the drum. Each row of suction cups corresponds to a row of carrier bar pockets. System changeover and cleaning can be accomplished very quickly with the quick-release drum and shoe mechanisms. The drum is removed by loosening the four clamping knobs on the drum support assembly and lifting the drum out of the support arm. A gear is located on the end of the drum which engages with a drive gear mounted inside the machine side frame. When the drum is clamped into place, it engages with the drive gear to synchronize with the carrier bar conveyor drive. A vacuum shoe is inserted through the inner bore of the eject drum. When the vacuum shoe handle is pushed inward, it will rotate a quarter-turn and lock in place. This locking mechanism includes a compression spring that is used to seal the shoe against the vacuum manifold, and a set of cam operated spring plungers and rollers to provide a seal against the inner drum surface.

It thus will be appreciated that the ejection system may work in conjunction with the vision inspection system. For example, in the event that the vision inspection system determines that the product is unacceptable according to predefined standards, a signal may be sent to the controller that, in turn, will relay another signal to activate the ejection system. A vacuum pump may be provided as a vacuum source. The amount of vacuum may depend on product characteristics. However, a a vacuum source capable of producing up to 60 in-$H_2O$ vacuum at 150 CFM free air flow (5 hp blower type recommended) may provide for proper operation of the automatic vision inspection defect removal system. Higher or lower power vacuum source(s) may be provided in different embodiments, of course. A female 2" barbed hose fitting may be provided, and a 230 VAC, Three Phase power outlet may be located at the rear of the machine to provide power to an external vacuum pump. A vacuum pump control button may be provided on the control panel to switch on or off the power to the auxiliary outlet. The number of vacuum solenoid valves may be selected based on the number of pockets in each row of the carrier bar. For instance, 24 vacuum solenoid valves may be used in certain examples. If a carrier bar for a particular set of change parts has less than 24 pockets, the remaining valves may be unused for that set of change parts. The system may be designed for fail-safe operation by "switching on" a valve to actively eject a product when the vision system identifies it as an acceptable product. When the inspection system classifies a product as a reject, the valve will be switched off and the product will remain in the carrier bar pocket until it is rejected off of the front of the conveyor using a blow tube. If there is a failure of a solenoid valve, or if the inspection system fails to send an accept signal, the product will go to the reject hold bin.

The ejection drum may be designed to match the pocket layout for a particular carrier bar. The drum may have soft, silicon vacuum suction cups to remove accepted product from each carrier bar pocket. The vacuum shoe may be mounted inside the ejection drum to channel vacuum to the row of suction cups above the carrier bar pockets with tablets as the bars move under the ejection drum. The reject blow-off tube may blow air on the carrier bar pockets to help ensure that a rejected tablet is ejected into the reject bin. The reject hold bin, in turn, collects all of the failed tablets, whereas the discharge chute feeds the accepted tablets into the storage drum.

Figure 21:
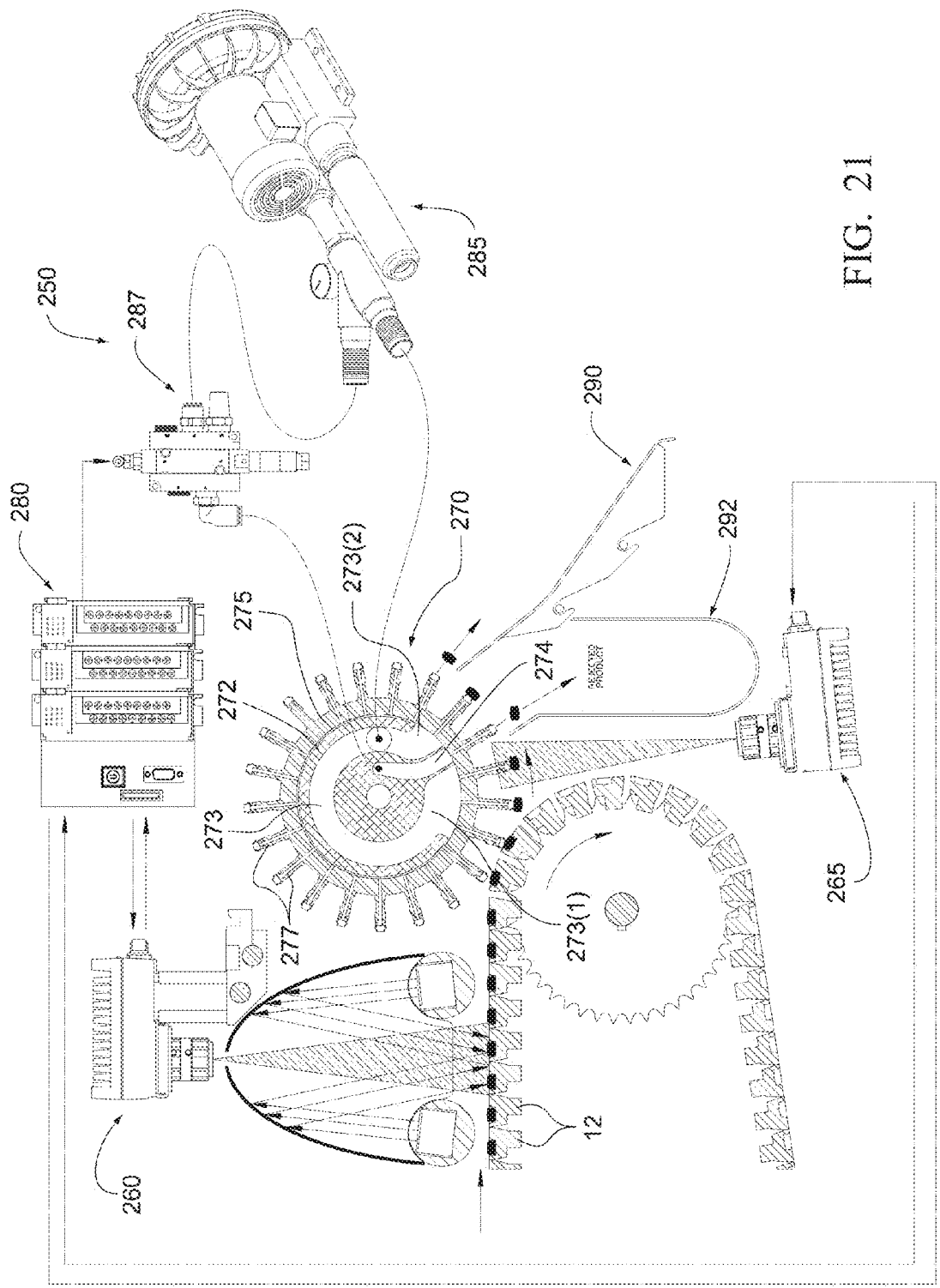
FIG. 21 is a schematic view of an inspection system according to another embodiment of the invention.

FIG. 21 illustrates a conveyer apparatus including an inspection system 250 according to another embodiment of the invention. In the previous embodiment, the inspection system determines whether one side of each article has been properly processed (e.g., marked), and then the removal unit passes the articles into "acceptable" or "defective" chutes. In the embodiment of FIG. 21, the inspection system determines whether both sides of each article have been properly processed, and then the removal unit passes the articles into "acceptable" or "defective" chutes.

The inspection system 250 includes a first camera unit 260, a second camera unit 265, a removal unit 270, and a controller 280. In use, one side of each article is inspected by the first camera unit 260 for one or more particular criteria or characteristics (e.g., marking error, printing misregistration, etc.), and then brought past the removal unit 270 configured to remove each article from the conveyer apparatus regardless of the results determined by the first camera unit. The removal unit carries the articles past the second camera unit 265 which inspects the other side of the articles for one or more particular criteria or characteristics. If both the first and second camera units determine that the article has met the particular characteristics, then that particular article is retained by the removal unit until it is discharged into the accepted product discharge chute 290. If one or both of the first and second camera units determine that the article has not met the particular characteristics, then that particular article is released by the removal unit and discharged into the rejected product discharge chute 292. Thus, the removal unit 270 removes all articles from the conveyer apparatus and selectively discharges the articles in response to signals from the first and second camera units 260, 265 into either the accepted product discharge chute 290 for acceptable articles that have met the particular characteristics or the rejected product discharge chute 292 for defective or flawed tablets that have not met the particular characteristics.

The first camera unit 260 (e.g., similar to the camera unit 60 described above) is positioned on an upper side of the conveyer apparatus to sense one side of the article, and the second camera unit 265 is positioned at the end of the conveyer apparatus to sense the other side of the article. As a result, both sides of the articles are sensed by the first and second camera units.

The first and second camera units provide signals to the controller 280, which signals the removal unit 270 so that specified articles can be discharged from the removal unit into the proper discharge chute.

In the embodiment of FIG. 21, the removal unit 270 includes a stationary vacuum shoe 272 and a product ejection drum 275 (with vacuum nozzles 277) rotatably mounted to the vacuum shoe. The vacuum shoe 272 includes a constant vacuum portion 273 communicated with a vacuum source 285, and a variable vacuum portion 274 communicated with the vacuum source via a controllable solenoid valve 287. The constant vacuum portion 273 includes a first portion 273(1) on one side of the variable vacuum portion 274 and a second portion 273(2) on the other side of the variable vacuum portion 274.

As the carrier bars pass below the drum 275, the nozzles 277 are communicated with the first portion 273(1) of the constant vacuum portion which allows the nozzles to remove (e.g., by suction) all the articles from respective pockets in the carrier bar. As the drum continues to rotate relative to the vacuum shoe, the nozzles will position the articles to be sensed by the second camera unit 265. Continued rotation of the drum moves the nozzles into communication with the variable vacuum portion 274. If an article is determined to be "acceptable" by both the first and second camera units 260, 265, the controller 280 signals the solenoid valve 287 to permit vacuum air to be applied to the selected variable vacuum portion 274 of the selected nozzle, which allows the selected nozzle to retain the individual article as it moves from communication with the variable vacuum portion 274 to the second portion 273(2) of the constant vacuum portion. Further rotation of the drum will move the nozzle out of communication with the second portion 273(2) of the constant vacuum portion and allow the article to eject or fall into the accepted product discharge chute 290. If an article is determined to be "defective", the controller signals the solenoid valve 287 to prevent vacuum air to be applied to the selected variable vacuum portion 274 of the selected nozzle. As a result, the defective article is released by the nozzle of the drum and is discharged or falls into the rejected product discharge chute 292.

Figure 22:
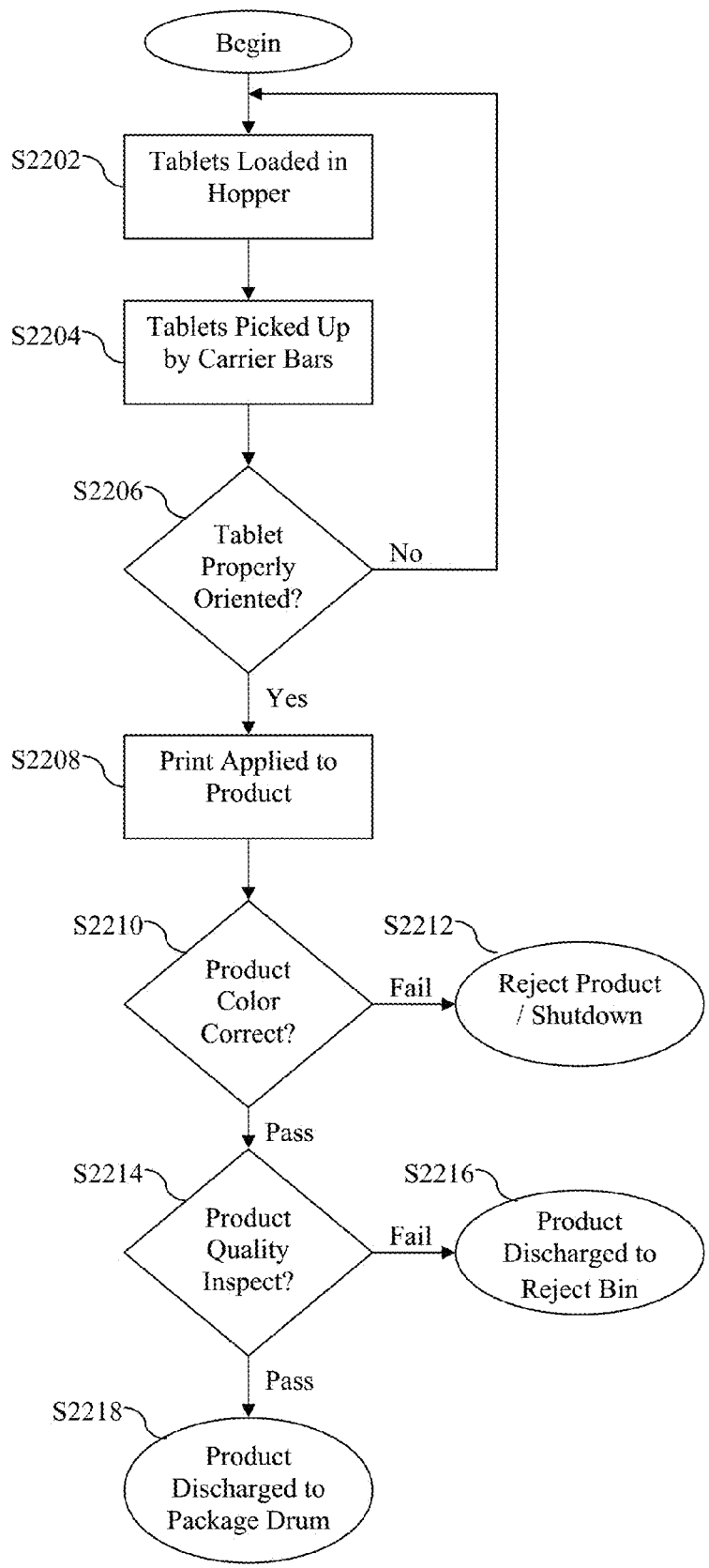
FIG. 22 is a flowchart providing an example of how of certain example embodiments may operate.

FIG. 22 is a flowchart providing an example of how of certain example embodiments may operate. In FIG. 22, tablets are loaded into the hopper in step S2202. At least some of the tablets are picked up by carrier bars in step S2204. A determination is made in step S2206 as to whether the tablets in the carrier bars are properly oriented. If they are not, some or all of the tablets in the carrier bar may be removed from the carrier bar and reloaded into the hopper, and processing may be returned to step S2202. One or more brushes may be provided for properly orienting the products in certain instances. If they are, however, then print may be applied to the product in step S2208. Any suitable technique may be used such as, for example, offset printing, inkjet printing, laser printing, gravure printing, etc. A determination is then made in step S2210 as to whether there are any color defects. If defects are detected, then the products with the defects are rejected or marked for rejection in step S2212 and/or the entire system may be shut down to investigate the cause of the problem. If there are no defects, however, the print quality is inspected in step S2214. Similar to the above defect test, if the product fails the product quality test, it may be discharged, e.g., to a reject bin in step S2216. If, however, the product passes, then it may be discharged to a package drum in step S2218.

In one or more steps not shown, a histogram tool may be used to check for the presence of products against the background of the carrier bar (e.g., light-colored tablets against a dark carrier bar). In some cases, to save processing time, the print quality check may be performed if and only if the histogram tool indicates that a product is present. Similarly, in certain example embodiments, where two or more stages of cameras are used, subsequent downstream processing may be performed if and only if prior tests are passed.

The print quality tests may be performed based on pattern matching and/or other suitable image or character recognition techniques in different embodiments. The image on the product may be detected regardless of its location and orientation in the carrier bar, thereby reducing the need for precision positioning of the tablet and/or camera. Individual features may be identified and isolated within an object image. For instance, characteristics such as shape, dimensions, angles, arcs, and/or shading may be identified. The spatial relationships between these identified features may be correlated with features from a trained image. The correlation may account for changes in distance and/or relative angle. By analyzing geometric information from both the features and spatial relationships, the object's position can be determined, potentially without regard to the object's angle, size, or appearance, in certain example instances.

After being initially trained with an image of a good quality printed table, the good image may be compared to the most recently acquired image. The quality of the recently acquired image may be rated based on the match. The location of the center of the printing on the product that was inspected may also determined to help ensure the logo is centered on the tablet, for example. Thus, the pattern recognition and trained image matching techniques of certain embodiments may be capable of detecting defects such as, for example, printed logo registration, incomplete printed logos, faded or blurry printed logos, double printed logos, etc. Cosmetic defect detection may also include, for example, chipped, capped, or broken products; coating defects, stains or specs; foreign object/rogue product detection, etc.

Damage inspection may involve checking to see if the product is broken, for example. A broken tablet typically shows up as several light-colored sections against a dark background. It therefore may be identified by using the vision system's "blob" tool, which looks for light-colored blobs smaller than the tablet. Coating defects also may be searched for and can sometimes be identified as a smaller white spot, because the core of the tablet is white. The blob tool also may be used to search for white spots.

In some embodiments, the camera acquires the image and performs each of these inspections and builds a binary word that contains the inspection results for each of the six tablets in its field-of-view. The vision system may send the results to the programmable logic controller (PLC) that runs the machine. The vision system also may in addition or in the alternative send each inspection image to the corporate network where it can be called up by the machine operators or engineers. A matrix of results may be maintained including, for example, a count of the number of defects at each position.

The PLC may operate a vacuum system that picks up the tablets from the carrier bar and moves them to a discharge chute, e.g., as described above. Based on the signal from the PLC, specific positions on the vacuum shoe are operated individually to either pick up or leave behind individual tablets. The tablets that have passed the inspection are picked up and placed in the discharge chute, while those that have failed remain in the carrier bar. In the next step, the tablets remaining in the carrier bar are dumped into a reject bin. This approach makes it possible to help reduce in a positive manner the number of individual tablets that fail inspection and ensure that only good tablets are passed along for packaging.

Figure 23:
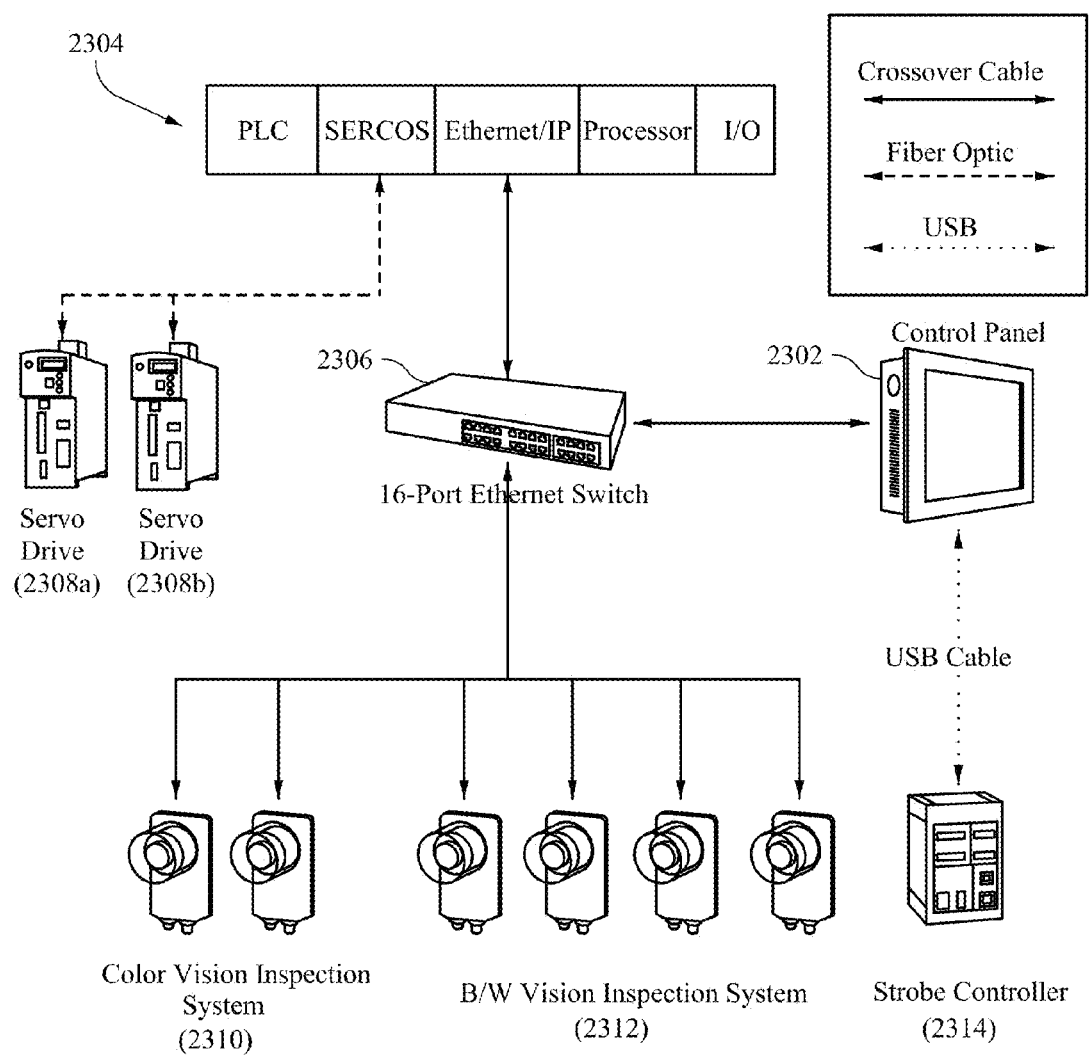
FIG. 23 is an example control system architecture according to an example embodiment.

An example control system architecture will now be described in connection with FIG. 23. A control panel 2302 provides an interface between the end-user/operator and the system. From the control panel 2302, the end-user may configure and operate the system according to various system parameters pre-programmed in connection with the underlying computer 2304. The computer 2304 includes several components. For example, a programmable logic controller (PLC) receives signals from inputs/outputs, as well signals from the control panel 2302. In certain examples, the PLC is the master control component of the system and contains the main system control software. The PLC, together with the processor and input/output (I/O) ports and Ethernet/IP connection, help coordinate components in the system. For instance, the PLC communicates with the control panel 2302 to provide an interface for the operator to monitor and/or configure the system settings for both the print and vision parameters. One or more servo drives (e.g., first and second servo drives 2308a and 2308b) in FIG. 23 communicate with the PLC to receive motion commands and provide position and velocity feedback to the PLC. The strobe controller 2314 may be setup through the control panel 2302 and may receive trigger signals from the cameras in either or both of the color vision inspection system 2310 and the black and white vision inspection system 2312. The cameras in the color vision inspection system 2310 and the black and white vision inspection system 2312, in turn, receive trigger signals from the PLC, and output an inspection result to the PLC tracking system. An Ethernet switch 2306 interconnects the control panel 2302, the computer 2304, the color vision inspection system 2310, and the black and white vision inspection system 2312. The connection between the strobe controller 2314 and the control panel 2302 may be a USB connection in certain examples, and the servo drives 2308a and 2308b may be connected to the servo controller of the computer 2304 with fiber optic cabling. Of course, other types of wired or wireless connections as between the various components and sub-components may be provided in different embodiments of the invention.

Recipes may be stored, e.g., in a non-transitory computer readable storage medium. The recipe information may include, for example, the number of carrier bars, the number of pockets per carrier bar, distance(s) between carrier bars and/or pockets, tolerance levels for defects, reference images, whether one or both types of cameras are to be used, reporting requirements, etc. Multiple recipes may be pre-stored or stored by the user/operator (e.g., for later use), thereby facilitating quick changeover. Each recipe may be uniquely identified in some cases.

In certain forms of the invention, the vision system may be a part of a distributed processing environment. The vision system may, for example, include one or more inspection stations that operate independent of each other, as alluded to above. In situations where a one-sided grayscale inspection is desired, a single inspection station may be used. In situations where two-sided inspection, or color and grayscale inspection are desired, two or more inspection stations may be used. Smart cameras are mounted adjacent to one another other in a row, above the carrier bars, and/or below the eject drum in the case of two-sided inspection. Each smart camera (sometimes referred to as a vision sensor) is responsible for inspecting an area of the carrier bar, and each camera contains a dedicated processor to perform its inspection task. This arrangement is advantageous for several reasons. For example, the camera's captured image data does not have to be sent over a cable to a central processing computer. This transfer of data, especially when there are multiple inspection stations, can cause a slower operating speed, e.g., to account for the time required to transfer the large amount of raw image data. With the smart cameras, the processing is performed within the camera, thereby changing the amount and type of data to be transferred. In certain instances, raw or processed image data need not be transmitted from the cameras, at all. Another advantage is that additional cameras can be added to the system without causing an increase in the overall processing time. Each smart camera contains its own dedicated processor, so cameras (and therefore processors) can be added to increase the speed and throughput of the system. By contrast, in some conventional arrangements, the addition of additional cameras actually slows processing. Still another advantage is that the cameras have much longer longevity without becoming obsolete as compared to an industrial computer. The fast obsolescence rate for computers can cause FDA validation problems if the exact same model is not available as a direct replacement for a failed computer, as some rules may specify that the replacement of an individual component must be accompanied by the certification of the replacement component and/or re-certification of the apparatus. Thus, an advantage of certain forms of the invention is that the self-contained vision system may be easily validated based on functionality alone. In some cases, the small package approach of providing a camera and image processing hardware and software enables a short validation procedure to be implemented, thereby making the upgrade to a new version of the vision system simple fairly straightforward from implementation and/or certification perspectives.

The following example components may be used in connection with certain embodiments. Of course, other components may be used in connection with different embodiments of this invention.

Touch-Screen Computer for control panel
    Specifications: Allen Bradley 6181F Integrated Display Computer, 17" Touch-Screen Monitor, Intel Core Duo 1.2 GHz Processor, 1 GB Dual-Channel DDR2 RAM, 24 VDC, Solid-State CompactFlash Drive
    Operating System: Microsoft Windows XP Professional SP2
    Software: Machine interface program and supporting DLL files developed by Ackley Machine Corporation using Microsoft Visual Basic 2010 version 10.0.30319.1
    Cognex In-Sight Explorer Camera Interface Program version 4.04.01
    Advanced Illumination Pulsar 320 Strobe LED Lighting Controller Interface Program version 1.0078125.2

Figure 24:
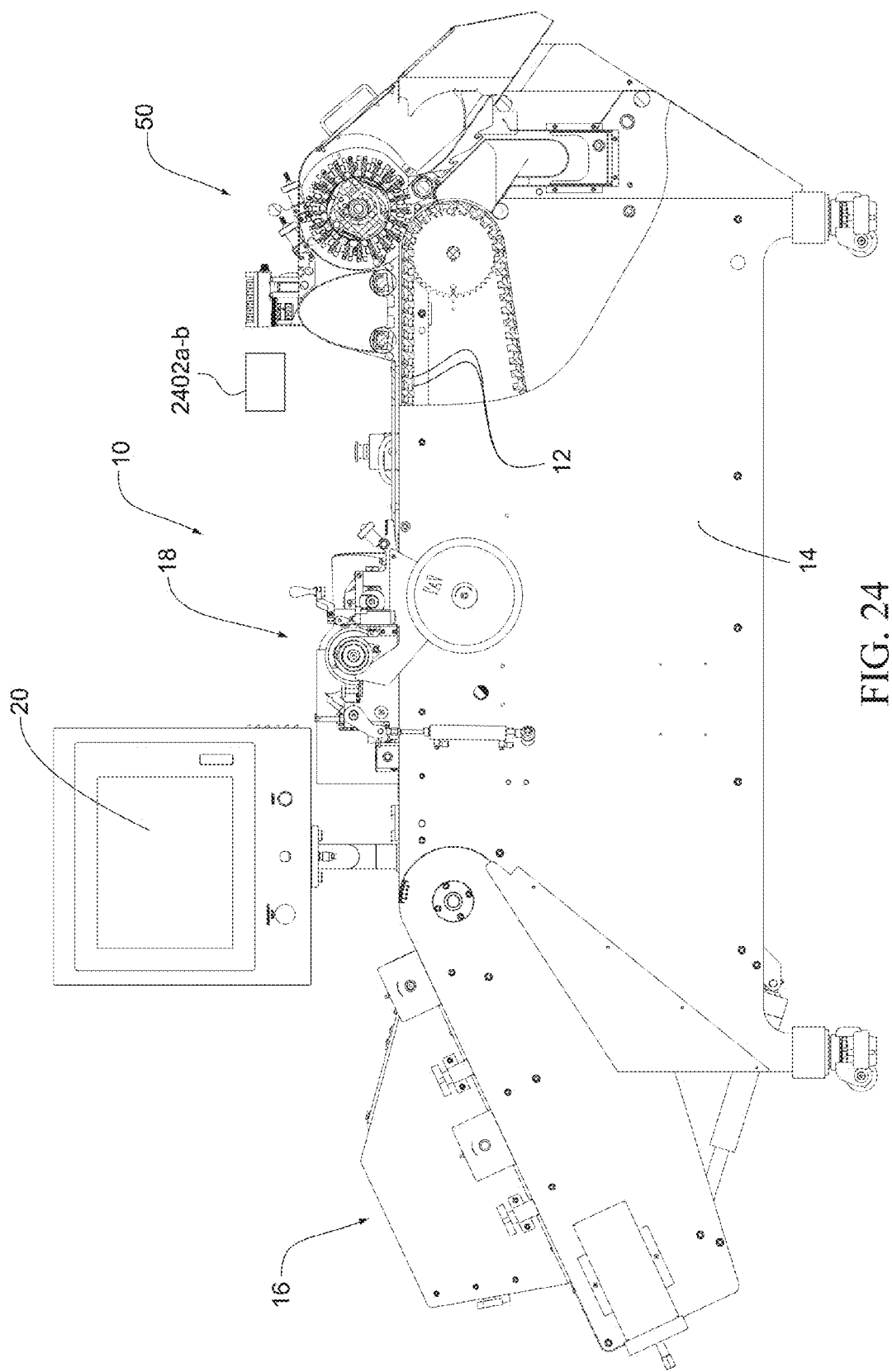
FIG. 24 is a side view of the conveyer apparatus of FIG. 1, with a portion of the apparatus shown in cross-section, modified to include additional cameras in accordance with an example embodiment.
Figure 25:
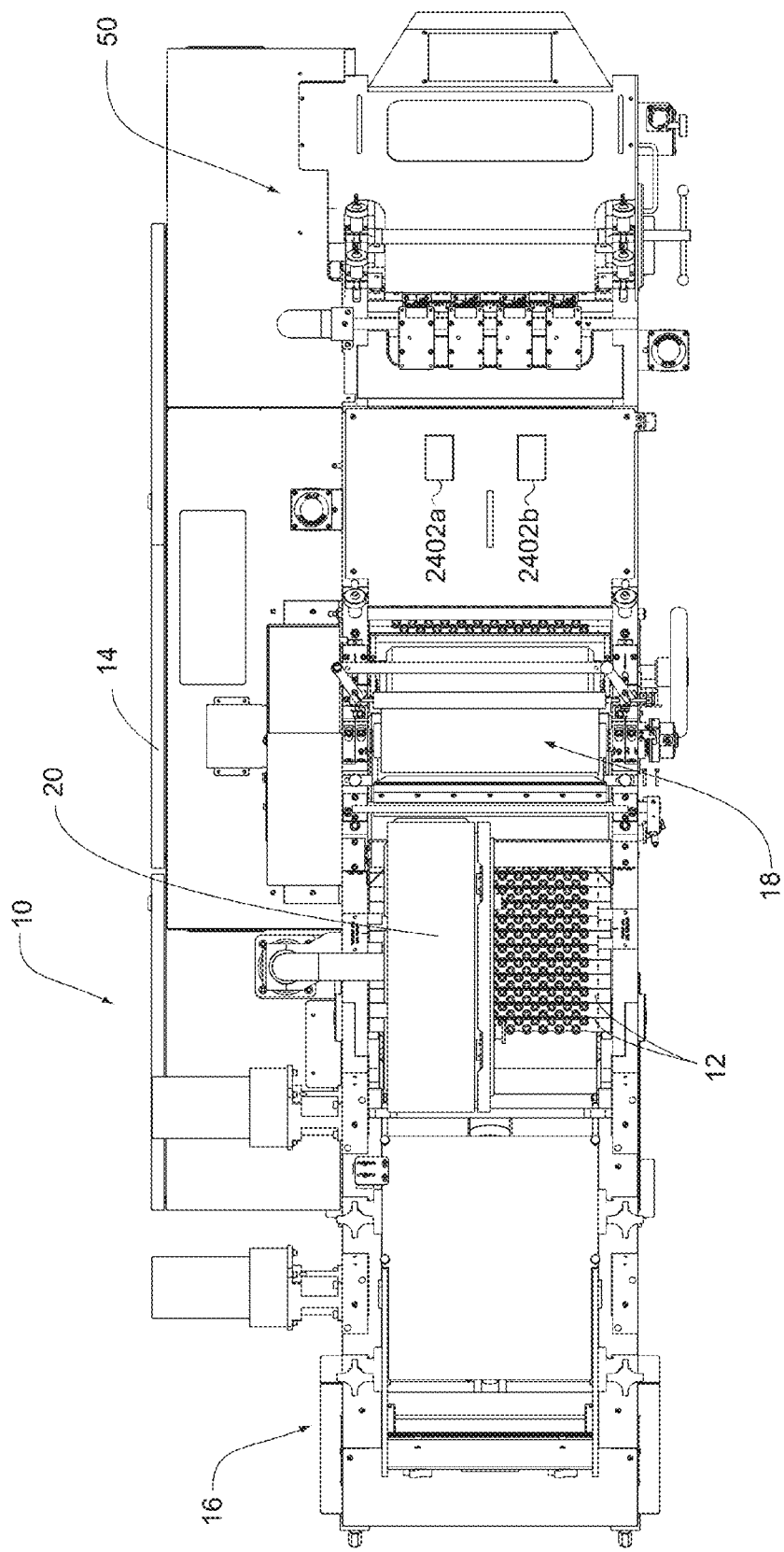
FIG. 25 is a top view of the conveyer apparatus of FIG. 24.

PLC Motion Controller
    Specifications: Allen Bradley 1768-L43 CompactLogix PLC, 2 MB Ram
    Firmware Revision: 17.3.59
    The PLC machine control program was created using Rockwell Automation RSLogix 5000 PLC Programming Software Control Panel Computer to PLC Communication
    The control panel computer communicates with the PLC via an Ethernet connection
    The control panel computer to PLC communication program and related support files were created using Cimquest INGEAR.NET Developer Edition Color Inspection Cameras
    Specifications: Cognex In-Sight 5400 Color Progressive Scan, 640×480 Resolution, 24 VDC
    Camera Firmware Version: 4.04.01
    Cameras are programmed using Cognex In-Sight Explorer software version 4.04.01
    Cameras are equipped with a full library of Cognex vision tools including PatMax Grayscale Inspection Cameras
    Specifications: Cognex In-Sight 5603 Progressive Scan, 1 GHz Processor, 1600×1200 Resolution, 24 VDC
    Camera Firmware Version: 4.04.01
    Cameras are programmed using Cognex In-Sight Explorer software version 4.04.01
    Cameras are equipped with a full library of Cognex vision tools including PatMax Camera to PLC Communication
    The cameras communicate with the PLC via Ethernet connection
    The camera to PLC communication program was developed using Cognex Connect AOP (Add-On Profile) to provide pre-configured device command outputs Camera to HMI Computer Communication: The cameras communicate with the HMI computer using standard Ethernet TCP/IP protocol FIG. 24 is a side view of the conveyer apparatus of FIG. 1, with a portion of the apparatus shown in cross-section, modified to include additional cameras in accordance with an example embodiment, and FIG. 25 is a top view of the conveyer apparatus of FIG. 24. FIGS. 24 and 25 are similar to FIGS. 2 and 3, except that multiple color cameras (first and second color cameras 2402a and 2402b) are provided upstream of the multiple black and white or grayscale cameras and substantially in line with one another. The vertical positioning may be the same or different as between the different types of cameras. The color cameras may be centered or substantially centered horizontally between the width of the black and white or grayscale cameras when there are more black and white or grayscale cameras than color cameras, and vice versa. Although the number of color cameras is one-half the number of black and white or grayscale cameras, different numbers and/or ratios may be provided in different embodiments. In addition, the centering or substantial centering need not always be true, as fewer cameras may be located at the extremities and possibly angled inwardly, offset to accommodate different structures or carrier bars, etc. Furthermore, the numbers of different types of cameras may be selected in part on the number of pockets in a row bar. Generally, the fewer pockets, the fewer cameras that may be provided. And generally, the higher the desired throughput, the more cameras that may be provided. In certain examples, one black and white or grayscale camera may service six pockets of a carrier bar, whereas one color camera may service 12 pockets of a carrier bar.

Figure 26:
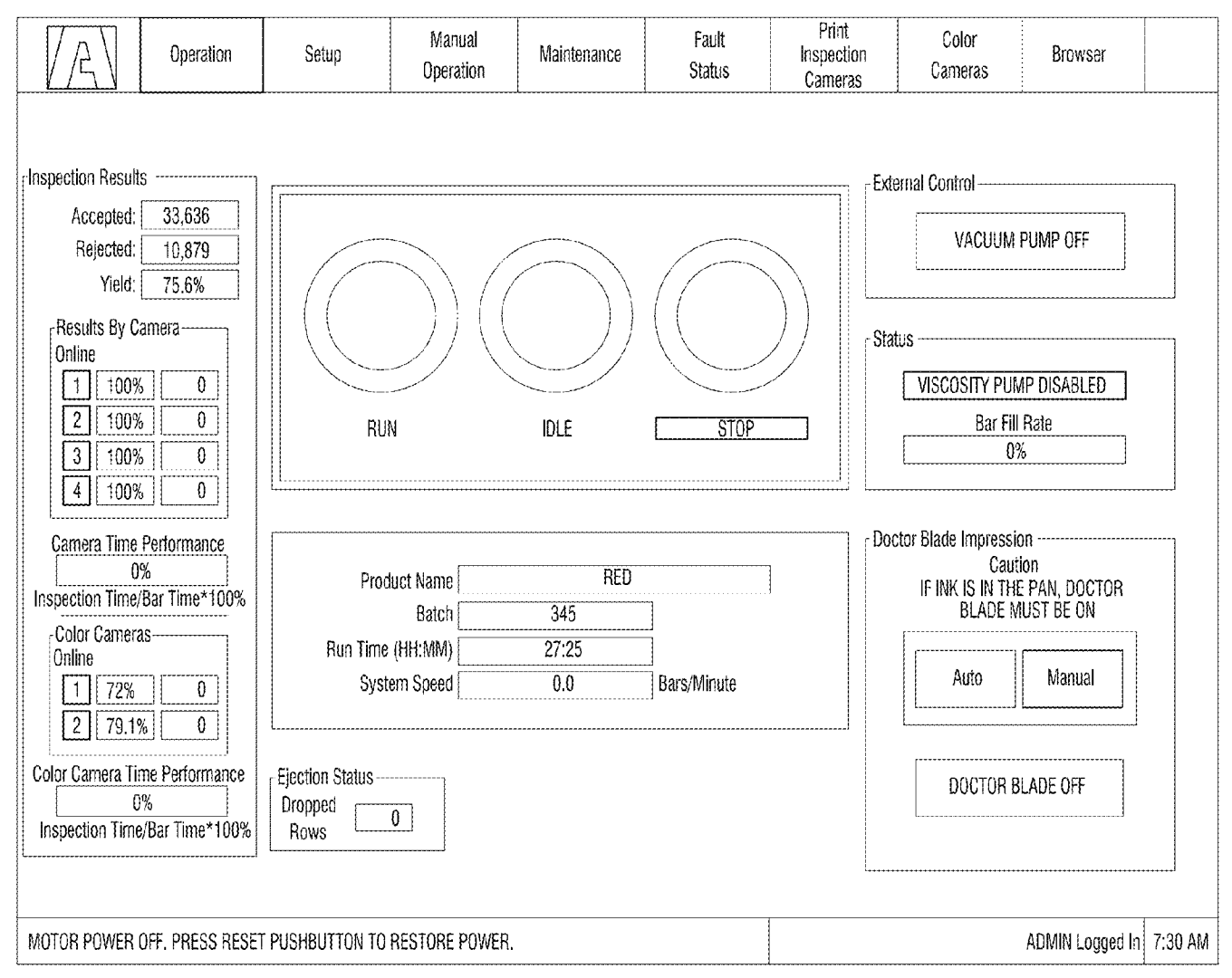

FIG. 26 is an example operation screen that may be displayed to a user/operator in accordance with an example embodiment. The left side of the example screen includes inspection result statistics including, for example, the total number of accepted and reject products, as well as the overall yield. A more detailed breakdown of results by camera (including yield per camera and dropped rows per camera) also is provided, and similar breakdowns may be provided as between the color versus black and white or grayscale cameras. Camera performance also may be shown according to calculated or raw metrics. For instance, camera time performance may be measured as inspection time divided by bar time*100%. The calculation may be performed since the last time the counters were reset. Empty pockets may or may not be included in this calculation. The overall status of the apparatus may be shown, e.g., in connection with a green/yellow/red stoplight type display (for running, idle, or stopped progress) and/or these may be functional buttons to cause the machine to run, idle, or stop, and basic details regarding the product (e.g., name), batch number or identifier, total run time, system speed (e.g., in terms of bars/minute, etc.), and ejection status (e.g., in terms of dropped rows) may be provided. Other information pertaining to whether the vacuum pump is on, whether the viscosity pump is enabled, whether the doctor blade is on (either in automatic or manual mode), what the bar fill rate percentage is, etc., also may be provided.

Figure 27:
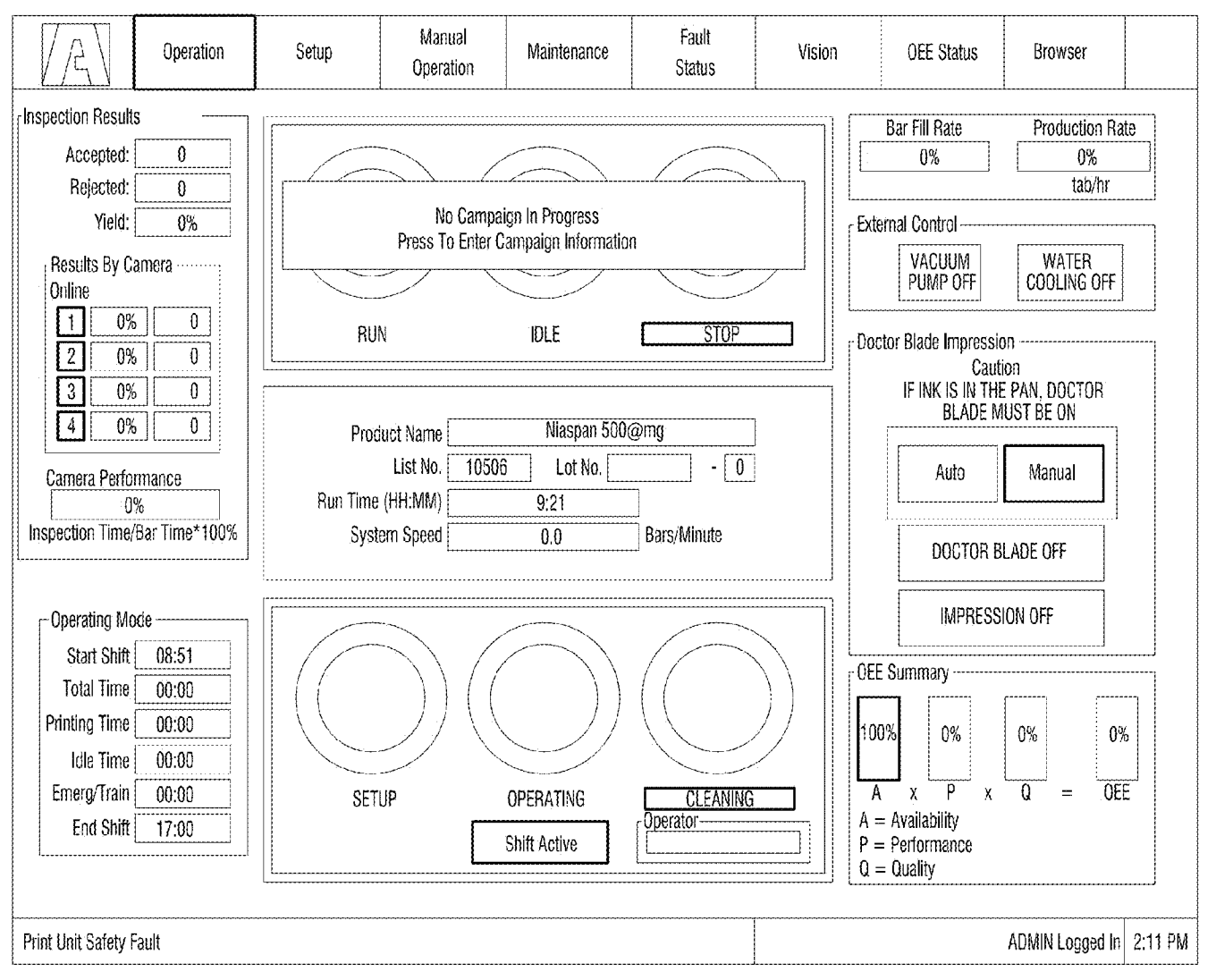

FIG. 27 is an example operation screen that includes overall equipment effectiveness (OEE) performance monitoring in accordance with an example embodiment. FIG. 27 is similar to FIG. 26. However, the overall efficiency of the printing system is also tracked through the OEE monitoring system and is displayed in FIG. 27. Real-time information is displayed relating to the availability, performance and quality ratings for each batch and/or shift.

Figure 28:
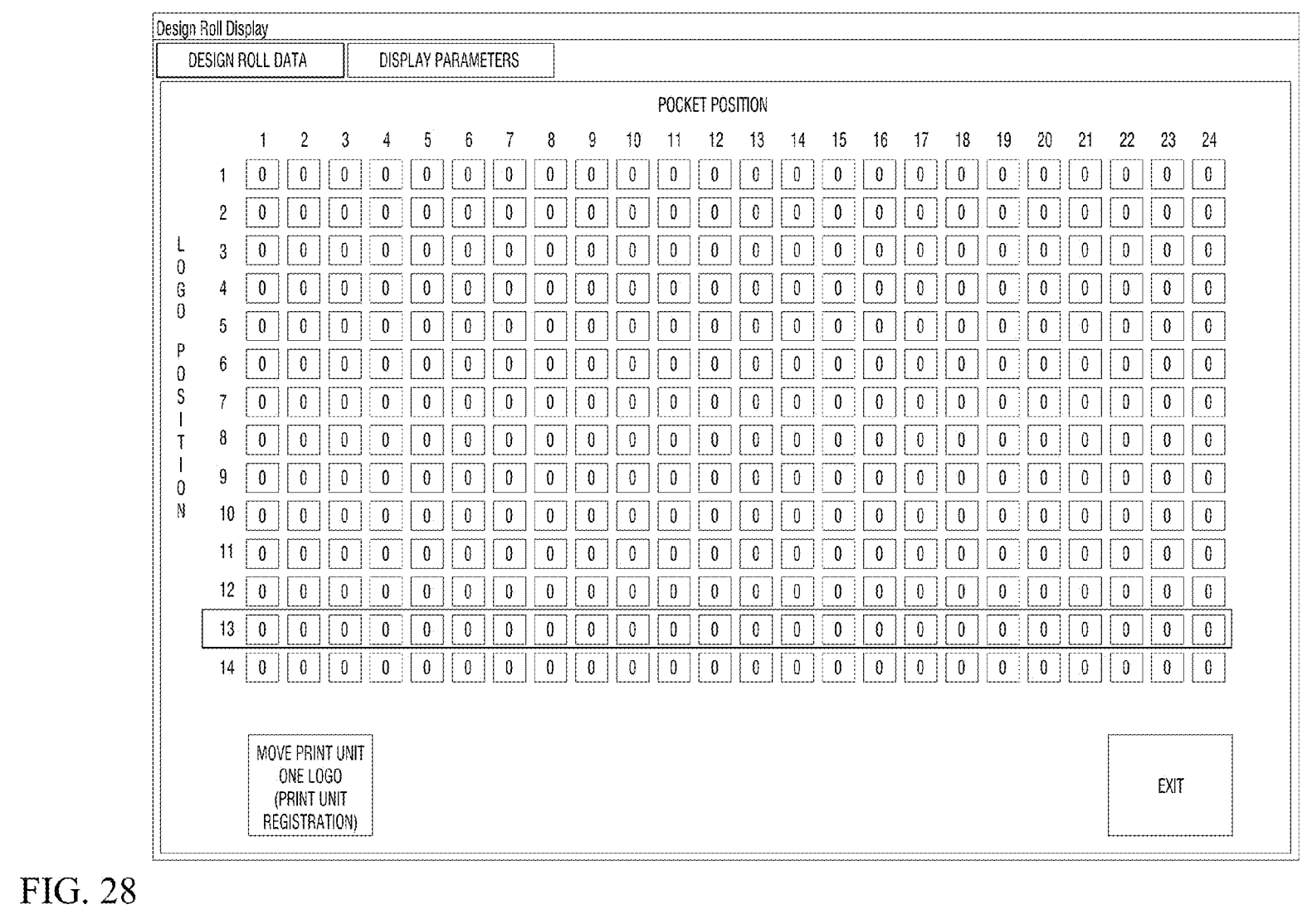

FIG. 28 is an example design roll data matrix screen in accordance with an example embodiment. The design roll data matrix screen displays a box for each etched logo contained on the design roll. The grid is shown as plotting logo position against pocket position. Inside each box, a number is displayed that tracks the total quantity of rejected product for logo defects from the corresponding etch on the design roll. This information can be used to diagnose the cause of detected defects and suggest possible solutions, thereby potentially reducing the number of defects and improve the process. For example, if a design roll etch is clogged with dried ink, there will be a greater number of defects originating from that etch on the design roll than the other non-clogged etches. This can be easily seen by looking at the matrix for abnormally large numbers in comparison with the other locations within the matrix. Another example is when the rubber offset roll has developed a flat surface, which occurs if the design roll is left on impression with the rubber offset roll for an extended period of time while the machine is not in operation. This type of defect can be easily seen in the matrix by looking for one or two rows of abnormally large defect numbers across the design roll (for example, two rows, such as rows 6 and 7—although not necessarily borne out in the FIG. 28 example screen). The grid may be generated, as the cameras are able to detect problems, while also keeping track of which pockets and which carrier bars the problems are in, which printers are implicated by the detected defects, as well as a time of the problem. Count data may be maintained by the cameras themselves and/or fed back to the PLC in certain implementations as they occur or in batch. It will be appreciated that in certain implementations, the data used to create the matrix may be the same or similar data as that involved in the vacuum pickup and selective depositing in the accept or reject areas.

In certain example embodiments, the selection of a particular part of the matrix may cause the relevant portions of the apparatus to become at least partially exposed. For instance, the design and/or rubber rolls may be rotated and/or raised so that a user/operator may visually inspect the areas that possibly have contributed to detected errors. In some cases, it may be possible to notice the wearing away of a portion of the design, a flattened or raised area of the rubber transfer roller, material stuck or lodged in various places, etc. A user/operator therefore may have an easier time diagnosing potential issues.

Figure 29:
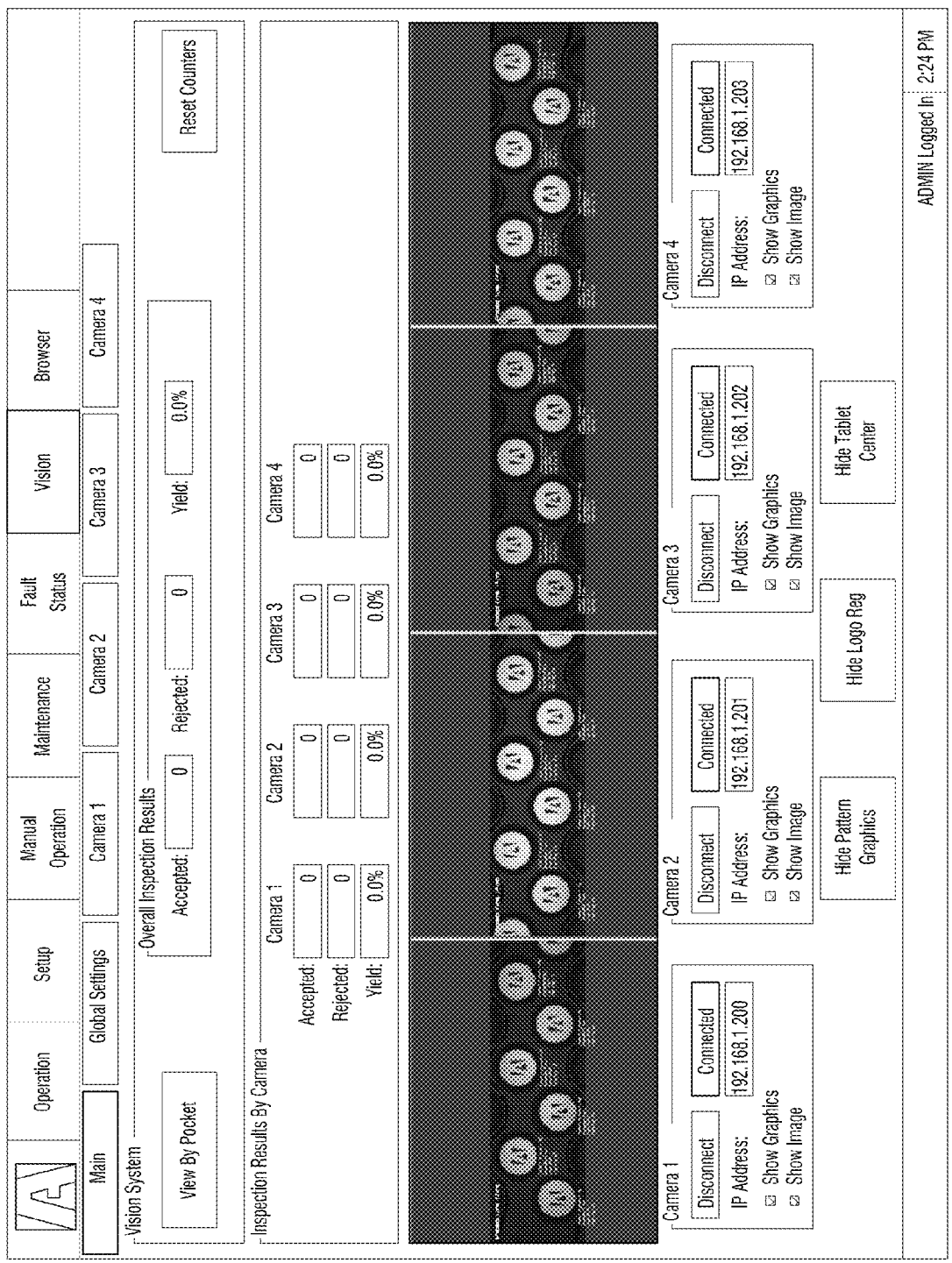
FIG. 29 is a screen that provides a single point of control for printing and vision system access in accordance with an example embodiment.

FIG. 29 is a screen that provides a single point of control for printing and vision system access in accordance with an example embodiment. The system's control panel or user interface may be hosted on a computer that includes a front-end program that communicates with control components on the machine. In certain implementations, all control components may be accessed and/or controlled via this program including, for example, all inspection cameras and lighting control. Similarly, in certain implementations, all setup parameters, system status information, and operational controls for both the printer and the automatic vision inspection may be contained within a single program (e.g., operating on a Windows XP based computer). On the vision screen, the real-time display window for each camera may be displayed across the screen to simulate the actual layout of the carrier bar. Each camera window may be zoomed-in to display a larger picture, and each camera may be controlled either individually through the camera tabs (e.g., manual trigger, live mode, etc.), or as a single inspection station through the global vision settings tab (e.g., overall inspection results, acceptance threshold settings, etc.). Pocket-by-pocket inspection results also may be provided, as may the overall accept/reject/yield data. The FIG. 29 example also includes the IP addresses of the cameras and their respective statuses (connected/disconnected).

Figure 30:
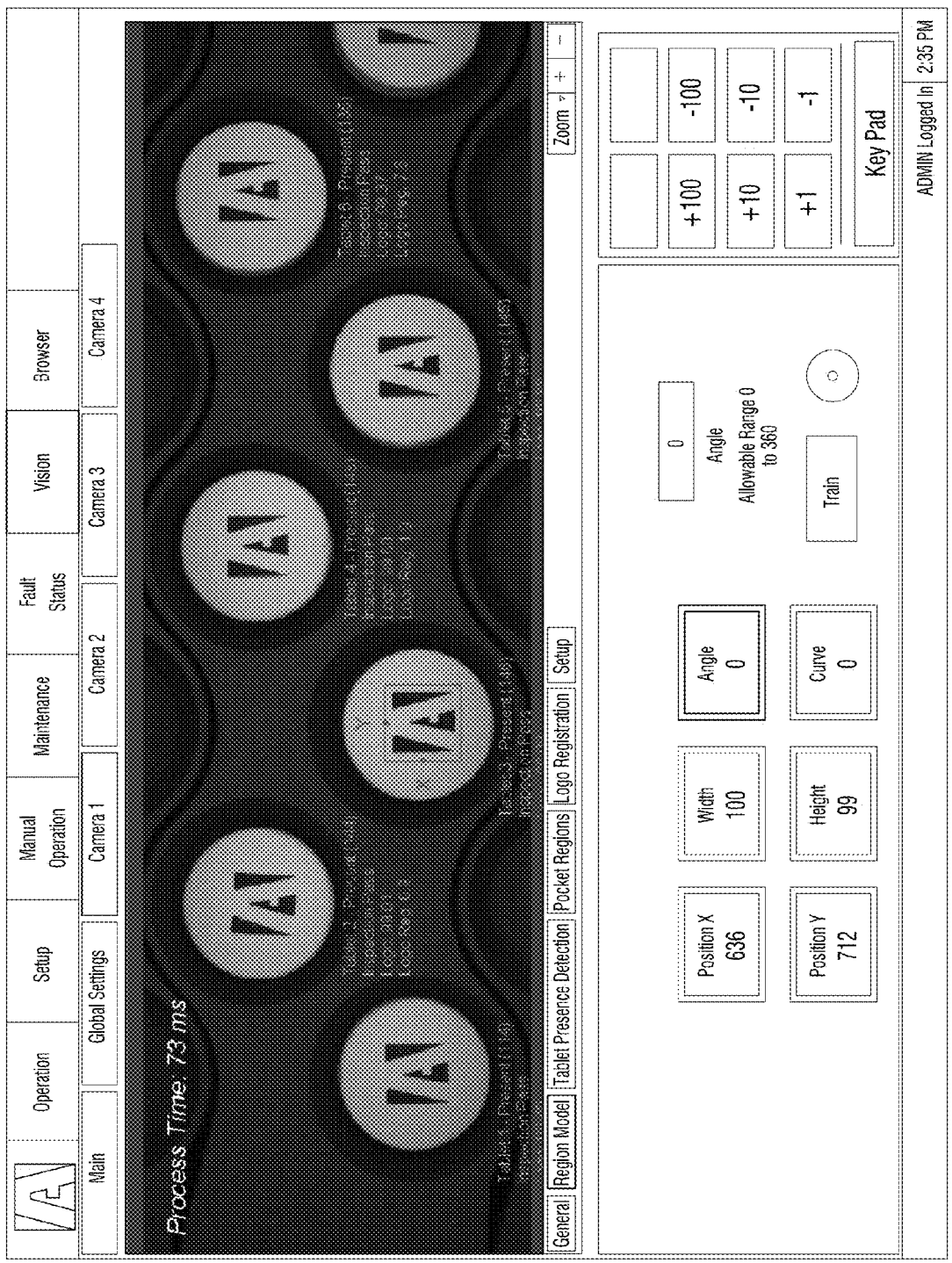
FIG. 30 is an example screen for vision system setup and logo training in accordance with an example embodiment.

FIG. 30 is an example screen for vision system setup and logo training in accordance with an example embodiment. The user interface may include controls to facilitate training of the logos and inspection regions for each camera. For instance, controls may be provided that allow the system to be trained specifically for print defect inspection, broken tablet inspection, coating defect inspection, etc. As shown in the FIG. 30 example screen, an enlarged view of a carrier bar is provided, with products located in its pockets. The user may initiate an automatic tablet presence detection and/or manually set or refine the detection so as to aid in training. For instance, a user may, for each pocket, specify the X and Y positions and/or distances of the logo, the angle at which the logo is offset relative to the cameras, etc. This training may be performed for each camera and/or globally. A digital image of the logo also may scanned for training purposes.

Search regions may be defined relative to the pockets and/or carrier bars. Cameras also may be physically positioned or repositioned to aid with recognition. In certain cases, a user/operator may train the system by placing a quality printed table in one of the pockets to be viewed by a first camera. A box may appear, enabling the user/operator to define the boundaries of the logo. This procedure may be repeated for each camera. Row and column graphic offsets may also be specified in certain example implementations.

Figure 31:
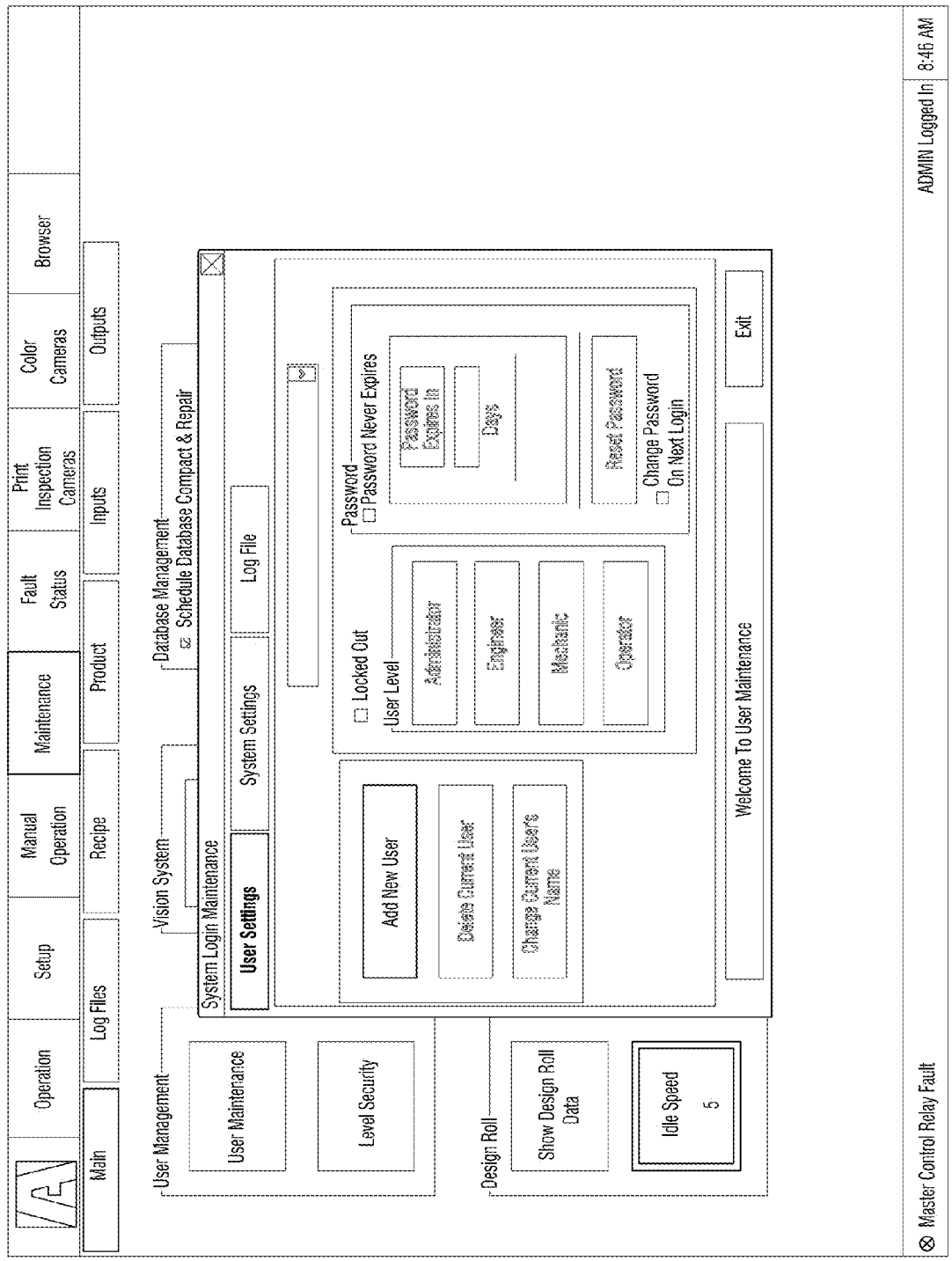

FIGS. 31 and 32 are example user maintenance screens in accordance with an example embodiment. The user interface may support multiple user logins. The users may have the same or different privileges. Thus, users may be added, deleted or modified. The password requirements and level of access for each user can be customized to meet any customer's standard procedures. For example, some users may have read-only access to the data, whereas other users may have the authority to change operating parameters, alter tolerance thresholds, initiate product changeovers, etc. Individual buttons or entire screens can be locked-down to prevent unauthorized users from accessing critical machine settings and/or functions. Predefined categories (e.g., administrator, engineer, mechanic, operator, etc.) may be provided, sometimes with default permissions, to suit the different operations. FIG. 32 in particular shows various screens and controls and enables permissions for the defined groups of users to be correspondingly set. Of course, it will be appreciated that other control mechanisms for these and/or other screens and/or features may be used in different embodiments.

Figure 33:
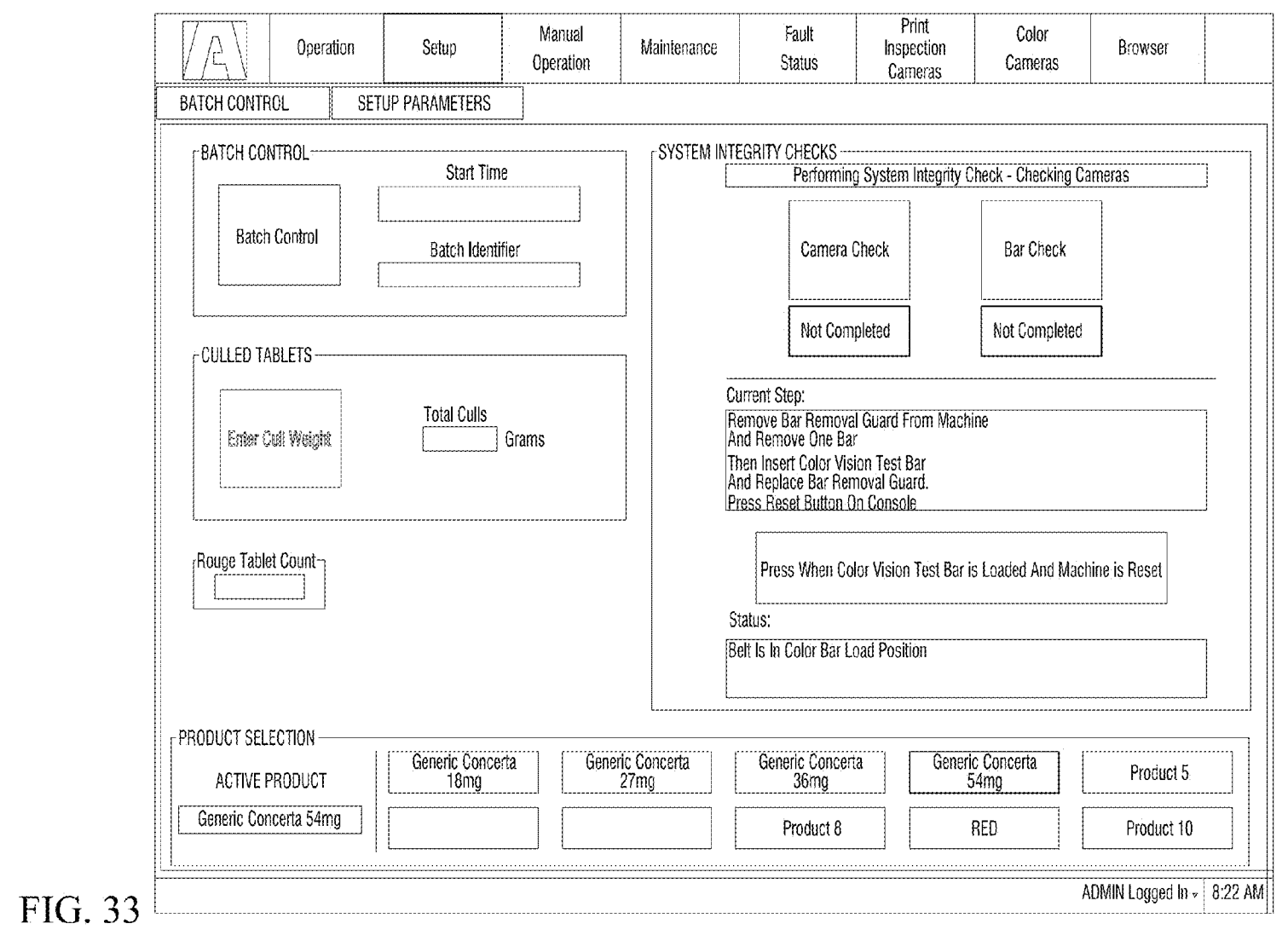

FIG. 33 is an example automatic vision system calibration verification screen in accordance with an example embodiment. A "calibration check" wizard may be provided. The wizard may in certain scenarios include on-screen instructions for the purpose of verifying that the cameras are calibrated correctly at the start of a batch. Specially designed carrier bars for both the color and grayscale cameras are conveyed underneath the cameras. The cameras capture high resolution images of the calibration bars, and compare the results with pre-set thresholds to determine if the cameras are properly calibrated. A bar check function may be provided to inspect each carrier bar installed along the conveyor, with the bar check function inspecting each bar to determine if it is the correct bar for the selected recipe, whether products are stuck in the carrier bar pockets, whether the carrier bars are installed in the correct orientation, etc. The wizard itself may walk the user through several ordered steps to ensure that the above and/or other aspects of the system are working properly.

Although certain example embodiments have been described herein as relating to tablets, it will be appreciated that the example techniques described herein may be applied to various other kinds of products such as, for example, pharmaceutical products, confectionery products, etc., which may be in tablet, capsule, soft-gel, and/or other forms. The example techniques described herein may accommodate various sizes and shapes of products including, for example, circular, ovular, oblong, square, rectangular, and/or other shapes. Furthermore, although certain example embodiments have been described as printing, the techniques described herein may be applied to other forms of processing. For instance, engraved or embossed patterns produced in other ways also may benefit from, for example, the example vision, tracking, and/or other techniques described herein. Dyed products also may benefit from the example techniques described herein. Errors or imperfections may be detected in other processing contexts in different forms of the invention. For instance, the techniques described herein may be applied downstream of any processing that might result in damage to a product such as, for example, chipping, breaking, flaking, smearing, smudging, etc., where logos, images, or other text is/are or is/are not involved.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. An inspection system, comprising:
    a conveyor to convey a plurality of pellet-shaped articles along a path;
    at least one camera oriented towards the conveyor so as to image the pellet-shaped articles being conveyed along the path;
    a removal unit, downstream from the at least one camera; and
    processing resources, including at least one processor and a memory, the memory including instructions executable by the at least one processor to control the inspection system to at least:
        process data received from the at least one camera to determine whether the pellet-shaped articles being imaged have a predetermined characteristic;
        responsive to a determination that a given one of the pellet-shaped articles has the predetermined characteristic, control the removal unit to remove the given one of the pellet-shaped articles that has the predetermined characteristic;
        generate, for output to a display device, operably connected to the inspection system, at least one display section including video output from the at least one camera, as the pellet-shaped articles are being imaged and as the data received from the at least one camera is being processed;
        receive input enabling a user to set a plurality of inspection regions, at least one of the inspection regions corresponding to an area internal to an outer boundary of a representative of the plurality of pellet-shaped articles and being defined by user-specification of a geometric shape superimposed on a displayed representation of the representative; and
        generate, for output to the display device, the geometric shape superimposed on the displayed representation of the representative.

2. The inspection system of claim 1, wherein the memory includes further instructions executable by the at least one processor to control the inspection system to at least provide an annotation relevant to the pellet-shaped articles that are being imaged for inclusion in the first display section.

3. The inspection system of claim 2, wherein the annotation includes an indication as to whether the pellet-shaped articles have the predetermined characteristic.

4. The inspection system of claim 2, wherein the annotation includes an indication as to whether the pellet-shaped articles have the predetermined characteristic, and at least one metric related to inspection for the predetermined characteristic.

5. The inspection system of claim 1, wherein the annotation includes a boundary of an image printed on the pellet-shaped articles.

6. The inspection system of claim 1, wherein the first display section includes real-time video output showing a plurality of the pellet-shaped articles.

7. The inspection system of claim 1, wherein a plurality of cameras are oriented towards the conveyor so as to image different areas of the conveyor and the pellet-shaped articles being conveyed along the path in those different areas of the conveyor.

8. The inspection system of claim 7, wherein the memory includes further instructions executable by the at least one processor to control the inspection system to at least generate, for output to the display device, different display sections including video output from the different cameras, as the pellet-shaped articles are being imaged and as the data received from the cameras is being processed, each display section corresponding to a different one of the plurality of cameras.

9. The inspection system of claim 8, wherein the different display sections are visible simultaneously on one display screen.

10. The inspection system of claim 8, wherein the display sections are enlargeable.

11. The inspection system of claim 1, wherein the memory includes further instructions executable by the at least one processor to control the inspection system to at least:
calculate inspection statistics based on input relating to the predetermined characteristic; and
generate for output to the display device a second display section including the calculated inspection statistics.

12. The inspection system of claim 11, wherein the input relating to the predetermined characteristic sensed by the at least one camera includes numbers of accepted and rejected pellet-shaped articles processed.

13. The inspection system of claim 11, wherein the inspection statistics include counts of the accepted and rejected pellet-shaped articles processed.

14. The inspection system of claim 11, wherein the inspection statistics include a calculated yield equal to the number of accepted pellet-shaped articles processed divided by the sum of the counts of the accepted and rejected pellet-shaped articles processed.

15. An inspection system, comprising:
a conveyor to convey a plurality of pellet-shaped articles along a path;
a plurality of cameras oriented towards the conveyor so as to image the pellet-shaped articles being conveyed along the path;
a removal unit, downstream from the plurality of cameras; and
processing resources, including at least one processor and a memory, the memory including instructions executable by the at least one processor to control the inspection system to at least:
process data received from the plurality of cameras to determine whether the pellet-shaped articles being imaged have a predetermined characteristic;
responsive to a determination that a given one of the pellet-shaped articles has the predetermined characteristic, control the removal unit to remove the given one of the pellet-shaped articles that has the predetermined characteristic;
generate, for output to a display device, operably connected to the inspection system, at least one display section including video output from the plurality of cameras, as the pellet-shaped articles are being imaged and as the data received from the at least one camera is being processed;
calculate inspection statistics based on input relating to the predetermined characteristic; and
generate for output to the display device a second display section including the calculated inspection statistics,
wherein at least some inspection statistics are calculated on a camera-by-camera basis.

16. The inspection system of claim 11, further comprising a plurality of cameras, wherein at least some inspection statistics include a system-wide yield of accepted pellet-shaped articles, and yields of accepted pellet-shaped articles on a camera-by-camera basis.

17. An inspection system, comprising:
a conveyor to convey a plurality of pellet-shaped articles along a path;
at least one camera oriented towards the conveyor so as to image the pellet-shaped articles being conveyed along the path;
a removal unit, downstream from the at least one camera; and
processing resources, including at least one processor and a memory, the memory including instructions executable by the at least one processor to control the inspection system to at least:
process data received from the at least one camera to determine whether the pellet-shaped articles being imaged have a predetermined characteristic;
responsive to a determination that a given one of the pellet-shaped articles has the predetermined characteristic, control the removal unit to remove the given one of the pellet-shaped articles that has the predetermined characteristic; and
generate, for output to a display device, operably connected to the inspection system, at least one display section including video output from the at least one camera, as the pellet-shaped articles are being imaged and as the data received from the at least one camera is being processed,
wherein the conveyor includes at least one row of product receiving pockets, the pockets being structured to convey the pellet-shaped articles along the path, and wherein the memory includes further instructions executable by the at least one processor to control the inspection system to at least calculate at least some inspection statistics on a pocket-by-pocket basis.

18. The inspection system of claim 1, wherein the removal unit includes a rotatable drum having a plurality of nozzles along its length, each nozzle being structured to selectively remove from the conveyor one article at a time, based at least in part on a signal received from the processing resources.

19. The inspection system of claim 18, wherein the removal unit is structured to remove articles from the conveyor by suction.

20. A method of operating an inspection system, the method comprising:
conveying a plurality of pellet-shaped articles along a path via a conveyor;
imaging the pellet-shaped articles being conveyed along the path, using at least one camera oriented towards the conveyor;
processing data received from the at least one camera to determine whether the pellet-shaped articles being imaged have a predetermined characteristic;

responsive to a determination that a given one of the pellet-shaped articles has the predetermined characteristic, controlling a removal unit to remove the given one of the pellet-shaped articles that has the predetermined characteristic, the removal unit being located downstream from the at least one camera;

generating, for output to a display device operably connected to the inspection system, at least one display section including video output from the at least one camera, as the pellet-shaped articles are being imaged and as the data received from the at least one camera is being processed;

receiving input enabling a user to set a plurality of inspection regions, at least one of the inspection regions corresponding to an area internal to an outer boundary of a representative of the plurality of pellet-shaped articles and being defined by user-specification of a geometric shape superimposed on a displayed representation of the representative; and generating, for output to the display device, the geometric shape superimposed on the displayed representation of the representative.

21. The method of claim 20, further comprising providing, for inclusion in the first display section, an annotation relevant to the pellet-shaped articles that are being imaged, the annotation including an indication as to whether the pellet-shaped articles have the predetermined characteristic, at least one metric related to inspection for the predetermined characteristic, and/or a boundary of an image printed on the pellet-shaped articles.

22. The method of claim 20, wherein a plurality of cameras are oriented towards the conveyor so as to image different areas of the conveyor and the pellet-shaped articles being conveyed along the path in those different areas of the conveyor.

23. The method of claim 22, further comprising generating, for output to the display device, different display sections including video output from the different cameras, as the pellet-shaped articles are being imaged and as the data received from the cameras is being processed, each display section corresponding to a different one of the plurality of cameras.

24. The method of claim 23, wherein the different display sections are visible simultaneously on one display screen.

25. The method of claim 20, further comprising:

calculating inspection statistics based on input relating to the predetermined characteristic; and generating for output to the display device a second display section including the calculated inspection statistics.

* * * * *